(12) United States Patent
Chen

(10) Patent No.: US 6,979,687 B1
(45) Date of Patent: Dec. 27, 2005

(54) THEOPHYLLINE-BASED SOLUBLE GUANYLYL CYCLASE ACTIVATORS KMUP-1 ANALOGUES ENHANCED CYCLIC GMP AND K+ CHANNEL ACTIVITIES ON RABBIT CORPUS CAVERNOSUM SMOOTH MUSCLE AND INTERCAVERNOUS PRESSURE ACTIVITIES

(75) Inventor: Ing-Jun Chen, 10F, No.148-95, Guang-Hwa 1st Rd., Kaohsiung (TW)

(73) Assignees: Ing-Jun Chen, (TW); Cho-Jan Liang, (TW)

( * ) Notice: Subject to any disclaimer, the term of this patent is extended or adjusted under 35 U.S.C. 154(b) by 153 days.

(21) Appl. No.: 10/256,115

(22) Filed: Sep. 27, 2002

(51) Int. Cl.[7] ............. A61P 15/10; C07D 473/06; C07D 473/08
(52) U.S. Cl. ............... 514/252.16; 514/263.34
(58) Field of Search ............. 514/252.16, 263.34; 544/267, 272

(56) References Cited

U.S. PATENT DOCUMENTS 4,543,254 A * 9/1985 Kaneko et al. ........ 514/252.16
4,564,617 A * 1/1986 Sugimoto et al. ...... 514/263.22

FOREIGN PATENT DOCUMENTS

JP       58/150511 A2 * 9/1983

OTHER PUBLICATIONS

Chemical Abstracts Document No. 100:85510, 1984.*
Avasthi, K.; Chandra, T,; Rawat, D. S.; Bhakuni, D. S., Indian Journal of Chemistry, Section B: Organic Chemistry Including Medicinal Chemistry, 35B(5), 437-40.*

(Continued)

Primary Examiner—Thomas C. McKenzie
(74) Attorney, Agent, or Firm—Birch, Stewart, Kolasch & Birch, LLP

(57) ABSTRACT

The invention pertains to theophylline (1-methyl, 3-methyl xanthine) and IBMX (1-methyl, 3-isobutyl xanthine) derivatives of formulas I and II:

where $R_1$ is —$CH_3$ or —$CH_2CH(CH_3)_2$, and $R_2$ is where $R_3$ and $R_4$ are independently selected from the group consisting of $OCH_3$, $CH_3$, $NO_2$, F, Cl, Br and I.

2 Claims, 16 Drawing Sheets

OTHER PUBLICATIONS

Jean-Christophe Roegel Psychopharmacology Institute For Research in Neuroscience and Psychiatry [retrieved on Nov. 1, 2004]. dated 2002 Retreived from the Internet http://www.forenap.asso.fr/ftdweb/efficacy_pharmacodynamics.htm>.

Anderson, "Pharmacology of Lower Urinary Tract Smooth Muscles and Penile Erectile Tissues," Pharmacological Reviews, vol. 45, No. 3, 1993, pp. 253-308.

Angulo et al., "Combination of Phentolamine and L-Arginine Or Sildenafil Synergistically Improves Neurogenic Relaxation Of Rabbit Corpus Cavernosum Smooth Muscle," Urology, vol. 57, No. 3, 2001, pp. 585-589.

Arnold et al., "Nitric oxide activates guanylate cyclase and increases guanosine 3':5'-cyclic monophosphate levels in various tissue preparations," Proc. Natl. Acad. Sci. USA, vol. 74, No. 8, Aug. 1977, pp. 3203-3207.

Beavo, "Cyclic Nucleotide Phosphodiesterases: Functional Implications of Multiple Isoforms," Biological Review, vol. 75, No. 4, Oct. 1995, pp. 725-748.

Christ et al., "Characterization of K Currents in Cultured Human Corporal Smooth Muscle Cells," Journal of Andrology, vol. 4, No. 15, Sep./Oct. 1993, pp. 319-328.

Feleder et al., "Endothelium-mediated and $N^{\circ}$-nitro-L-arginine methyl ester-sensitive responses to cromakalim and diazoxidein the rat mesenteric bed," European Journal of Pharmacology, vol. 319, 1997, pp. 229-238.

Galle et al., "Effects of the soluble guanylyl cyclase activator, YC-1, on vascular tone, cyclic GMP levels and phsphodiesterase activity," British Journal of Pharmacology, vol. 127, 1999, pp. 195-203.

Garcia et al., "Charbdotoxin and its effects on potassium channels," Invited Review, 1995, pp. C1-C10.

Goldstein et al., "Oral Sildenafil in the Treatment of Erectile Dysfunction," The New England Journal of Medicine, vol. 338, No. 20, May 14, 1998, pp. 1397-1404.

Khan et al., "Coronary Vasorelaxation by Nitroglycerin: Involvement of Plasmalemmal Calcium-Activated $K^+$ Channels and Intracellular $CA^{++}$ Stores," Journal of Pharmacology and Experimental Therapeutics, vol. 284, No. 3, 1998, pp. 838-846.

Kim et al., "A Nitric Oxide-Like Factor Mediates Nonadrenergic-Noncholinergic Neurogenia Relaxation of Penile Corpus Cavernosum Smooth Muscle," J. Clin. Invest., vol. 88, Jul. 1991, pp. 112-118.

Kilpatrick et al., "Evidence for differential roles of nitric oxide (NO) and hyperpolarization in endothelium-dependent relaxation of pig isolated coronary artery," J. Pharmacol., vol. 112, 1994, pp. 557-565.

Kubo et al., "Atrial Natriuretic Factor and Isosorbide Dinitrate Modulate the Gating of ATP-Sensitive $K^+$ Channels in Cultured Vascular Smooth Muscle Cells," Circulation Research, vol. 74, No. 3, Mar. 1994, pp. 471-476.

Li et al., "Effect of Selective Inhibition of Soluble Guanylyl Cyclase on the $K_{Ca}$ Channel Activity in Coronary Artery Smooth Muscle," 1997, pp. 303-308.

Lin et al., "KMUP-1 relaxes rabbit corpus cavernosum smooth muscle in vitro and in vivo: involvement of cyclic GMP and $K^+$ channels,"British Journal of Pharmacology, No. 135, 2002, pp. 1159-1166.

Lin et al., "Xanthine-Analog, KMUP-2, Enhances Cyclic GMP and $K^+$ Channel Activities in Rabbit Aorta and Corpus Cavernosum With Associated Penile Erection," Drug Development Research, vol. 55, 2002, pp. 162-172.

Lowenstein et al., "Nitric Oxide: A Physiologic Messenger," vol. 120, No. 3, Feb. 1994, pp. 227-237.

McAuley et al., "Intracavernosal Sildenafil Facilitates Penile Erection Independent of the Nitric Oxide Pathway," Journal of Andrology, vol. 22, No. 4, Jul./Aug. 2001, pp. 623-628.

Medina et al., "Inhibition of neuroeffector transmission in human vas deferens by sildenafil," British Journal of Pharmacology, vol. 131, 2000, pp. 871-874.

Miyamoto et al., "Bronchodilator Activity of Xanthine Derivatives Substituted with Functional Groups at the 1- or 7-Position," J. Med. Chem, vol. 36, 1993, pp. 1380-1386.

Moncada et al., "Nitric Oxide: Physiology, Pathophysiology, and Pharmacology," Pharmacological Review, vol. 43, No. 2, 1991, pp. 109-141.

Moreland et al., "$PGE_1$ Suppresses the Induction of Collagen Synthesis By Transforming Growth Factor-$\beta_1$ in Human Corpus Cavernosum Smooth Muscle," Journal of Urology, vol. 153, 1995, pp. 826-834.

Murphy et al., "Apamin-sensitive K+ channels mediate an endothelium-dependent hyperpolarization in rabbit mesenteric arteries," Journal of Physiology, vol. 489, No. 3, 1995, pp. 723-734.

Murphy et al., "Nitric oxide hyperpolarizes rabbit mesenteric arteries via ATP-sensitive potassium channels," Journal of Physiology, vol. 486, No. 1, 1995, pp. 47-58.

Nelson et al., "Physiological roles and properties of potassium channels in arterial smooth muscle," Invited Review, 1995, pp. C799-C822.

Park et al., "Sildenafil Inhibits Phosphodiesterase Type 5 in Human Clitoral Corpus Cavernosum Smooth Muscle," Biochemical and Biophysical Research Communications, vol. 249, 1998, pp. 612-617.

Perez-Vizcaino et al., "Role of $K^+$ channel opening and stimulation of cyclic GMP in the vasrelaxant effects of nicorandil in isolated piglet pulmonary and mesenteric arteries: relative efficacy and interactions between both pathways," British Journal of Pharmacology, vol. 123, 1998, pp. 847-854.

Rehman et al., "Intracavernous Pressure Responses to Physical and Electrical Stimulation of the Cavernous Nerve in Rats," Urology, vol. 51, No. 4, 1998, pp. 640-644.

Saito et al., "Does potassium induce the release of nitric oxide in the rabbit corpus cavernosum?" Urol Res, vol. 26, 1998, pp. 137-141.

Seyam et al., "Evaluation of a No-Needle Penile Injector: A Preliminary Study Evaluating Tissue Penetration and its Hemodynamic Consequences in the Rat," Urology, vol. 50, No. 6, 1997, pp. 994-998.

Sobey et al., "Inhibitory effect of 4-aminophyridine on response of the basilar artery to nitric oxide," British Journal of Pharmacology, vol. 126, 1999, pp. 1437-1443.

Soderling et al., "Regulation of camp and cGMP signaling: new phosphodiesterases and new functions," Current Opinion in Cell Biology, vol. 12, 2000, pp. 174-149.

Stasch et al., "NO-independent regulatory site on soluble guanylate cyclase," Nature, vol. 410, Mar. 8, 2001, pp. 212-215.

Stief et al., "The Effect of the Specific Phosphodiesterase (PDE) Inhibitors on Human and Rabbit Cavernous Tissue In Vitro and In Vivo," Journal of Urology, vol. 159, Apr. 1998, pp. 1390-1393.

Trigo-Rocha et al., "The Role of Cyclic Adenosine Monophosphate, Cyclic Guanosine Monophosphate, Endothelium and Nonadrenergic, Noncholinergic Neurotransmission in Canine Penile Erection," Journal of Urology, vol. 149, Apr. 1993, pp. 872-877.

Wallis et al., "Tissue Distribution of Phosphodiesterase Families and the Effects of Sildenafil on Tissue Cyclic Nucleotides, Platelet Function, and the Contractile Responses of Tabeculae Carneae and Aortic Rings in Vitro," American Journal of Cardiology, vol. 83, No. 5A, Mar. 4, 1999, pp. 3C-12C.

Wang et al., "Nitric Oxide Mediates Penile Erection in Cats," Journal of Urology, vol. 151, Jan. 1994, pp. 234-237.

Weidelt et al., "Acetylcholine-induced $K^+$ currents in smooth muscle cells of intact rat small arteries," Journal of Physiology, vol. 500, No. 3, 1997, pp. 617-630.

White et al., "Endothelium and cannbinoid receptor involvement in levcromakalim vasorelaxation," European Journal of Pharmacology, vol. 339, 1997, pp. 157-160.

Wohlfart et al., "Release of nitric oxide from endothelial cells stimulated by YC-1, an activator of soluble quanylyl cyclase," British Journal of Pharmacology, vol. 128, 1999, pp. 1316-1322.

Wu et al., "A xanthine-based KMUP-1 with cyclic GMP enhancing and $K^+$ channels opening activities in rat aortic smooth muscle," British Journal of Pharmacology, vol. 134, 2001, pp. 265-274.

Wu et al., "C-1 inhibited human platelet aggregation through NO-independent activation of soluble guanylate cyclase," British Journal of Pharmacology, vol. 116, 1995, pp. 1973-1978.

Wu et al., "The mechanism of actions of 3-(5'-(hydroxymethyl-2'-furyl)-1-benzyl indazole (YC-1) on $Ca^{2+}$-activated $K^+$ currents in $GH_3$ lactotrophs," Neuropharmacology, vol. 39, 2000, pp. 1788-1799.

Abstract, Juilfs et al., "Cyclic GMP as substrate and regulator of cyclic nucleotide phosphodiesterases (PDEs)," Rev. Physiol. Biochem. Pharmacol., vol. 135, 1999, pp. 67-104.

Abstract, Lee et al., "Characterization of ATP-sensitive potassium channels in human corporal smooth muscle cells," Int. J. Impot. Res. vol. 11, No. 4, Aug. 1999, pp. 179-188.

Abstract, Lue, "The mechanism of penile erection in the monkey," Semin. Urol. vol. 4, No. 4, Nov. 1986, pp 217-224.

Abstract, Martinez-Pineiro et al., "New features of pharmacologic treatment of erectile dysfunction," Arch Esp. Urol., vol. 49, No. 3, Apr. 1996, pp. 270-276.

Abstract, Nakagawa et al., "Possible increases in potassium conductance by apamin in mammalian ventricular papillary muscles: a comparison with the effects on enrymatically isolated ventricular cells," J. Cardiovasc. Pharmacol., vol. 14, No. 1, Jul. 1989, pp. 38-45.

Abstract, Schmidt et al., "The nitric oxide and cGMP signal transduction system: regulation and mechanism of action," Biochem. Bophys. Acta., Aug. 18, 1993, pp. 153-175.

Abstract, Wu et al., "A xanthine-based KMUP-1 with cyclic GMP enhancing and K (+) channels opening activities in rat aortic smooth muscle," Br. J. Pharmacol, vol. 134, No. 2, Sep. 2001, pp. 265-274.

* cited by examiner

THEOPHYLLINE-BASED SOLUBLE GUANYLYL CYCLASE ACTIVATORS KMUP-1 ANALOGUES ENHANCED CYCLIC GMP AND K+ CHANNEL ACTIVITIES ON RABBIT CORPUS CAVERNOSUM SMOOTH MUSCLE AND INTERCAVERNOUS PRESSURE ACTIVITIES

FIELD OF THE INVENTION

This invention relates to compounds of theophylline based KMUP-1 and KMUP-2 (KMUPs), which upon laboratory testing on animals, have proven that they pharmacologically possesses action on endothelium-dependent NO releasing, soluble guanynyl cyclase (sGC) activation, minimum phosphodiesterase (PDE) inhibition, $K^+$-channel opening, relaxation of corpus carvernosal smooth muscle, increase of intracarvernosal pressure ($\Delta$ICP), and enhanced learning and memory activities.

BACKGROUND OF THE INVENTION

Inhibition of type 4 phosphodiesterase (PDE) by xanthine derivatives, including methylxanthine, such as theophylline, usually increases intracellular formation of cyclic AMP in various smooth muscle cells. Among them, theophylline is tranditionaly a non-selective PDE (phosphodiesterase) inhibitor (Beavo et al. *Physiol Rev.*, 75, 725–748, 1995).

KMUP-1, a theophylline-based derivative, has been described to have not only minimum PDE (phosphodiesterase) inhibition but also enhanced cyclic GMP (guanosine 3',5'-cyclic monophosphate) increasing activities in previous report (WU, B. N. et al. *Br. J. Pharmacol.*, 134, 265–274, 2001). Type 5 PDE (phosphodiesterase) inhibitor such as sildanafil, with cyclic GMP (guanosine 3',5'-cyclic monophosphate) increasing activity, has proved to be effective in the treatment of penile dysfunction after its oral administration in man (Goldstein I. et al. *N. Engl. J. Med.*, 338, 1397–1404, 1998). However, KMUP-1, with minimum PDE (phosphodiesterase) inhibition as YC-1 but also with NO-releasing, and NO-independent sGC activation activity, similar to YC-!, to increase cyclic GMP activities in rat aortic smooth muscle, was thus supposed similarly to have rabbit cavernosal smooth muscle relaxation and penile erection effects in this invention.

Activation of soluble guanyl cyclase (sGC) induces the formation of cyclic GMP (guanosine 3',5'-cyclic monophosphate), which is a second messenger of NO action, generally modulates the activity of its effector proteins that lead to vasorelaxation (Schmidt T. et al. *Biochim. Biophys. Acta.*, 1178, 153–175, 1993) and also the opening of $K^+$-channel (Murphy M. E. and Brayden, J. E. *J. Physiol.*, 489, 723–734, 1995). It is reasonable to suggest that activation of sGC (soluble guanylyl cyclase) and inhibition of phosphodiesterase (PDE) that metabolize the cyclic GMP (guanosine 3',5'-cyclic monophosphate), may together attribute to the increase of cyclic GMP associated vascular and cavernosal smooth muscle relaxations. YC-1 is a representative of this class of NO (nitric oxide)-independent sGC activator with PDE inhibition and may lead to a long-lasting cyclic GMP-mediated inhibition of vasoconstriction (Wu C. C. et al. *Br. J. Pharmacol.*, 116, 1973–1978, 1995; Galle J. et al., *Br. J. Pharmacol.*, 127, 195–203, 1999). Recently, BAY 41-2272 and BAY 51-9491 potently activate sGC (soluble guanylyl cyclase) by a mechanism that is also NO-independently (Stasch et al. *Nature.*, 410, 212–215, 2001). KMUP-1 is thus suggested to have YC-1 like activity but having different chemical structure, characteristicly with theophylline base.

DESCRIPTION OF THE PRIOR ART

To date, sildenafil has been described to abolish vas deferens contractility initiated by K channel blocker (Medina et al. *Br. J. Pharmacol.*, 131, 871–874., 2000); YC-1 mediate stimulation of $Ca^{2+}$-$I_{K(Ca)}$ and effectively inhibited the voltage-dependent $K^+$ current $I_{K(V)}$ in $GH_3$ lactotrophs (Wu et al *Neuropharmacology.*, 39, 1788–1799., 2000). In contrast, KMUP-1 displayed not only minimum inhibition of PDE (phosphodiesterase) and enhanced activation of sGC (soluble guanylyl cyclase), but also reversed the $K^+$ channel blockade caused by $K^+$ channel blockers in rat aortic smooth muscle (Wu et al., *Br. J. Pharmacol.*, 134, 265–274.2001).

$K^+$ channel openers, acting by liberation of NO (nitric oxide), have been shown to relax human isolated CCSMs (corpus cavernosum smooth muscle) and produce erection when injected intracoiporeally into animals and men (Saito et al *Urol. Res.*, 26, 137–141, 1998). Many experimental animals have been employed in in vivo studies of penile erection (Rehman J. et al., *Urology.*, 51, 640–644, 1998; Seyam R. M. et al., *Urology.*, 50, 994–998, 1997; Trigo-Rocha et al., 1993; Lue, T. F. *Semin. Urol.*, 4, 217–224, 1986; Wang R. et al., *J. Urol.*, 151, 234–237, 1994; Stief C. G. et al., *J. Urol.*, 159, 1390–1393, 1998). KMUP-1, a methyl xanthine and piperazine derivative, structurally with 6 nitrogen atoms as sildenafil and with an ethylpiperazine moiety on the position 7 of theophylline-base, combining the PDE (phosphodiesterase) inhibition, sGC (soluble guanylyl cyclase) stimulation, and $K^+$ channels opening activity, has been described to achieve the full relaxation activity in rat aortic smooth muscle (Wu B. N. et al., *Br. J. Pharmacol.*, 134, 265–274, 2001). Taking above consideration, we are thus encouraged to use KMUP-1, multiply with above effects in vasculature, to examine its possible effects in rabbit CCSM and penile erection, including associated $K^+$-channel opening activity.

In this invention, we characterized the effects of KMUP-1 on rabbit CCSMs (corpus cavernosum smooth muscles) and associated NO/sGC/cGMP activation, retard of induced $K^+$ channels blocking, and PDE (phosphodiesterase) inhibiting activities. Notable was found in erectile dysfunction that associated with vascular relaxation, the combination use of PDE inhibitor and sGC (soluble guanylyl cyclase) stimulator or $K^+$-channel opener was suggested to enhance the results achieved (Notable Martinez-Pineiro et al. *Arch. Esp. Urol.*, 49, 270–276.,1996). KMUP-1, with those possible activities and intracavernous pressure (ICP) increasing effect, is suggested to be hopeful in the management of erectile dysfunction.

SUMMARY OF THE INVENTION

This invention relates to KMUP-1 and KMUP-2, which upon laboratory testing on animals, have proven that they pharmacologically possesses NO releasing from endothelium, sGC activation on smooth muscle, minimum type Five phosphodiesterase inhibition, relaxation of corpus carvernosal smooth muscle, and increase of intracarvernosal pressure ($\Delta$ICP). Both relaxation of KMUP-1, KMUP-2 were attenuated by endothelium removed, high $K^+$ and pretreatments with soluble guanylyl cyclase (sGC) inhibitors ODQ, a NOS inhibitor L-NAME, a $K^+$ channel blocker TEA, a $K_{ATP}$ channel blocker glibenclamide, a voltage-dependent $K^+$ channel blocker 4-AP and $Ca^{2+}$-dependent $K^+$ channel blockers apamin and charybdotoxin. The relaxant responses of KMUP- 1 together with a standard PDE (phosphodiesterase) inhibitor IBMX (3-isobutyl, 1-methyl xanthine) had additive actions on rabbit corpus cavernosum smooth muscle.

BRIEF DESCRIPTION OF THE DRAWINGS

The invention will now be described by way of example with reference to the accompanying Tables and Figures in which:

Scheme 1 Compound A synthesis scheme

Table 1 The physicochemical Data of N7-substituted theophylline

Table 2 Peak increased intracavernous pressure ($\Delta$ICP) and duration of tumescence response to KMUP-1 and sildenafil (n=8)

Figure 1:
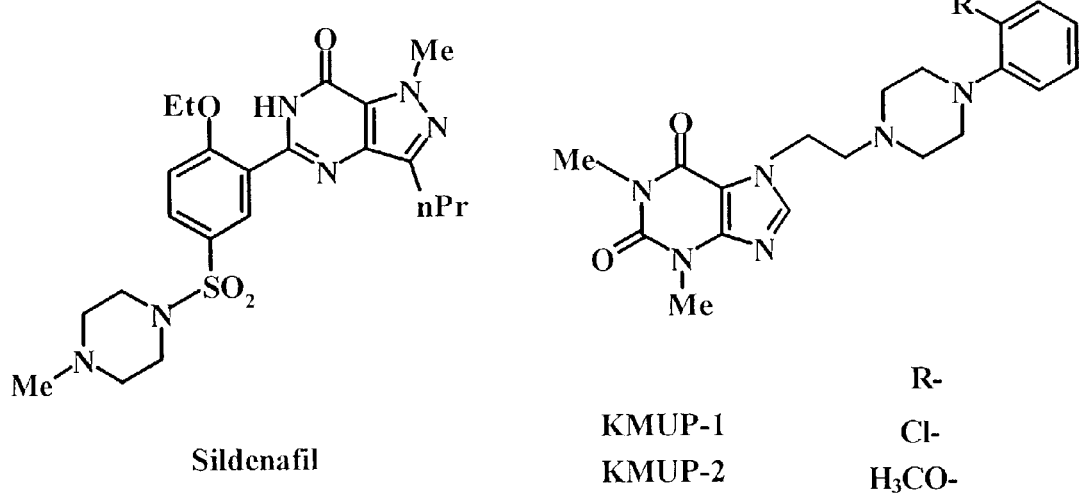

FIG. 1 Chemical structures of KMUP-1, KMUP-2 and sildenafil

Figure 2:
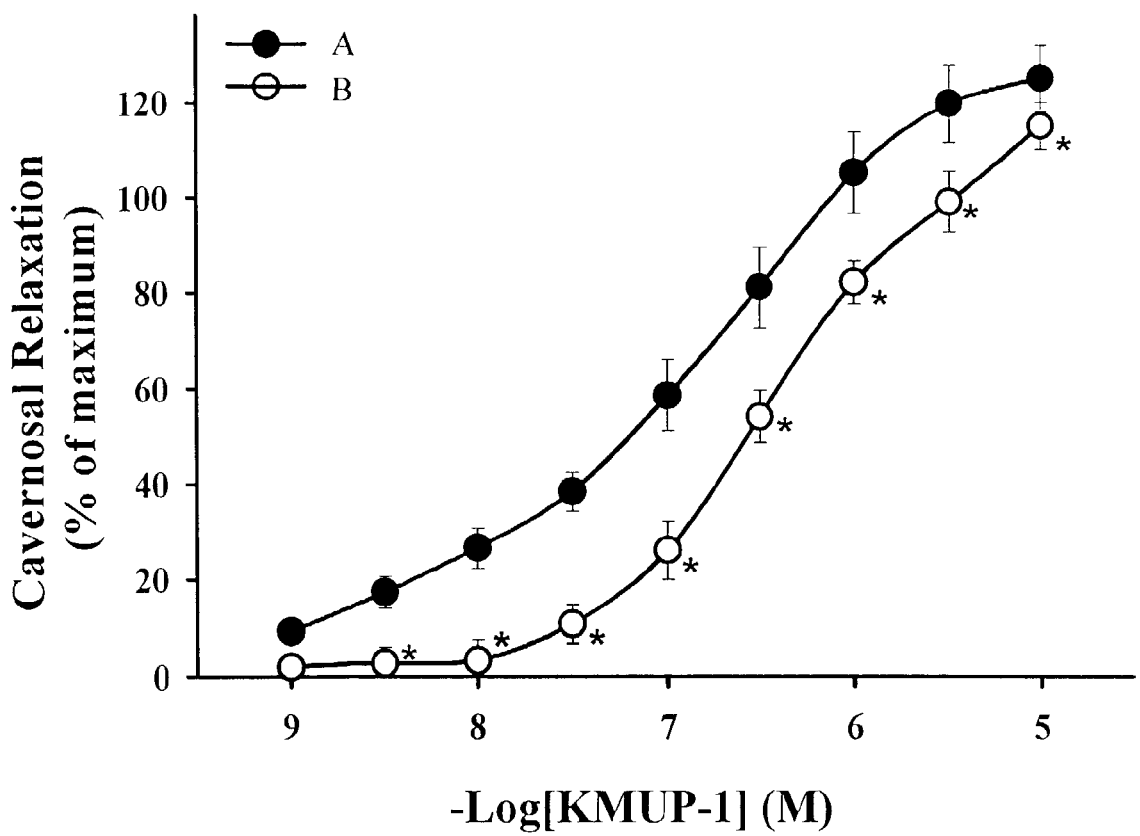

FIG. 2 Effects of KMUP-1 on phenylephrine (10 $\mu$M)-precontracted rabbit corpus cavernosum in the endothelium-denuded EC (−) and endothelium-intact EC (+) corporeal smooth muscle strips. *P<0.05, n=12 as compared with the KMUP-1 (two way repeated measures ANOVA followed by Student-Newman-Keuls test).
   A . . . EC (+)
   B . . . EC (−)

Figure 3:
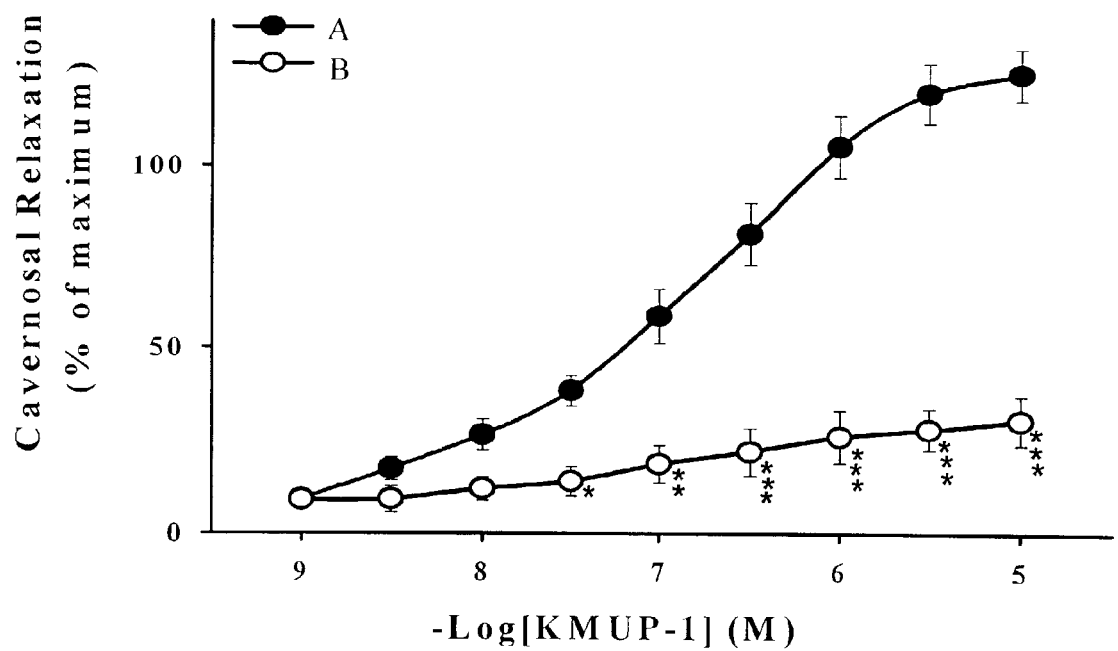

FIG. 3 Effects of KMUP-1 on the rabbit corpus cavernosum, precontracted with phenylephrine (10 $\mu$M) and 60 mM KCl, respectively. *P<0.05, P<0.01, *P<0.001, n=12 as compared with the KMUP-1 (two way repeated measures ANOVA followed by Student-Newman-Keuls test).
   A . . . Phenylephrine (10 $\mu$M)
   B . . . KCl (60 mM)

FIG. 4 Effects of KMUP-1 (A) and sildenafil (B) on phenylephrine-precontracted rabbit corpus cavernosum in the absence and presence of potassium channel blockers.

Figure 4A:
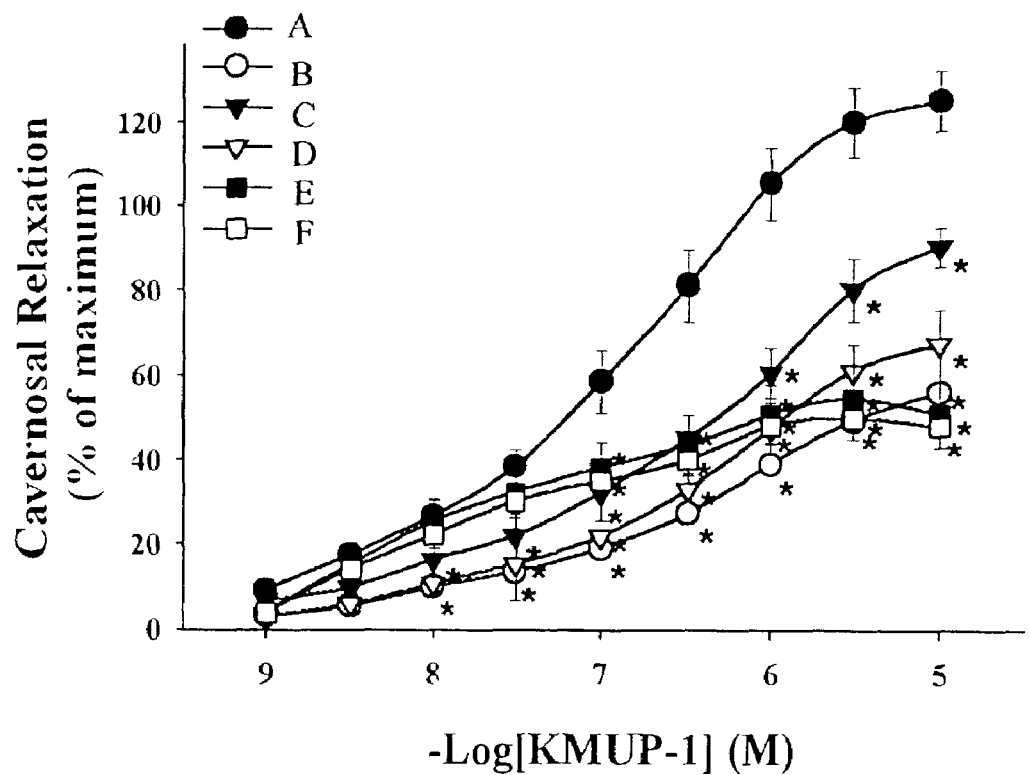

FIG. 4(A) Effects of KMUP-1 on phenylephrine (10 $\mu$M)-precontracted rabbit corpus cavernosum in the absence and presence of potassium channel blockers. *P<0.05, n=12 as compared with the KMUP-1 (two way repeated measures ANOVA followed by Student-Newman-Keuls test).

FIG. 3 Effects of KMUP-1 on the rabbit corpus cavernosum,
   *P50.05, n=12 as compared with the KMUP-1 (two way repeated measures ANOVA followed by Student-Newman-Keuls test).

Figure 4B:
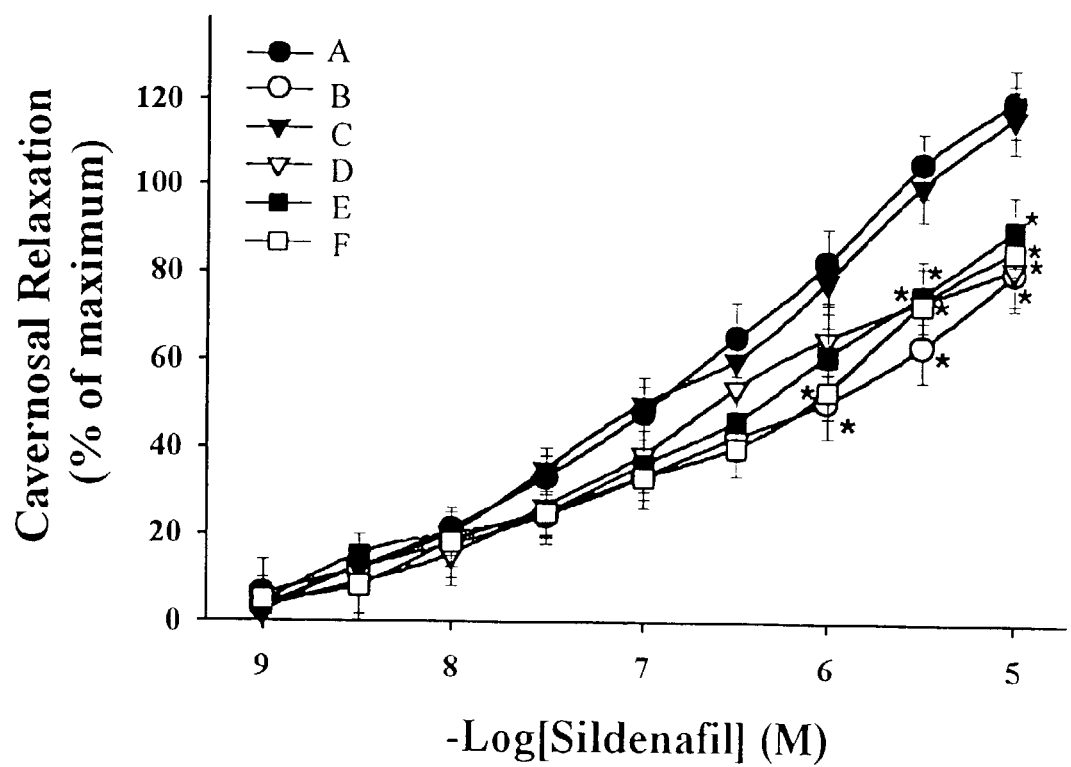

FIG. 4(B) Effects of sildenafil on phenylephrine (10 $\mu$M)-precontracted rabbit corpus cavernosum in the absence and presence of potassium channel blockers. *P<0.05, n=12 as compared with the KMUP-1
   A . . . control
   B . . . after TEA (10 mM)
   C . . . after glibenclamide (1 $\mu$M)
   D . . . after 4-AP (100 $\mu$M)
   E . . . after apamin (1 $\mu$M)
   F . . . after charybdotoxin (ChTX, 0.1 $\mu$M).

Figure 5A:
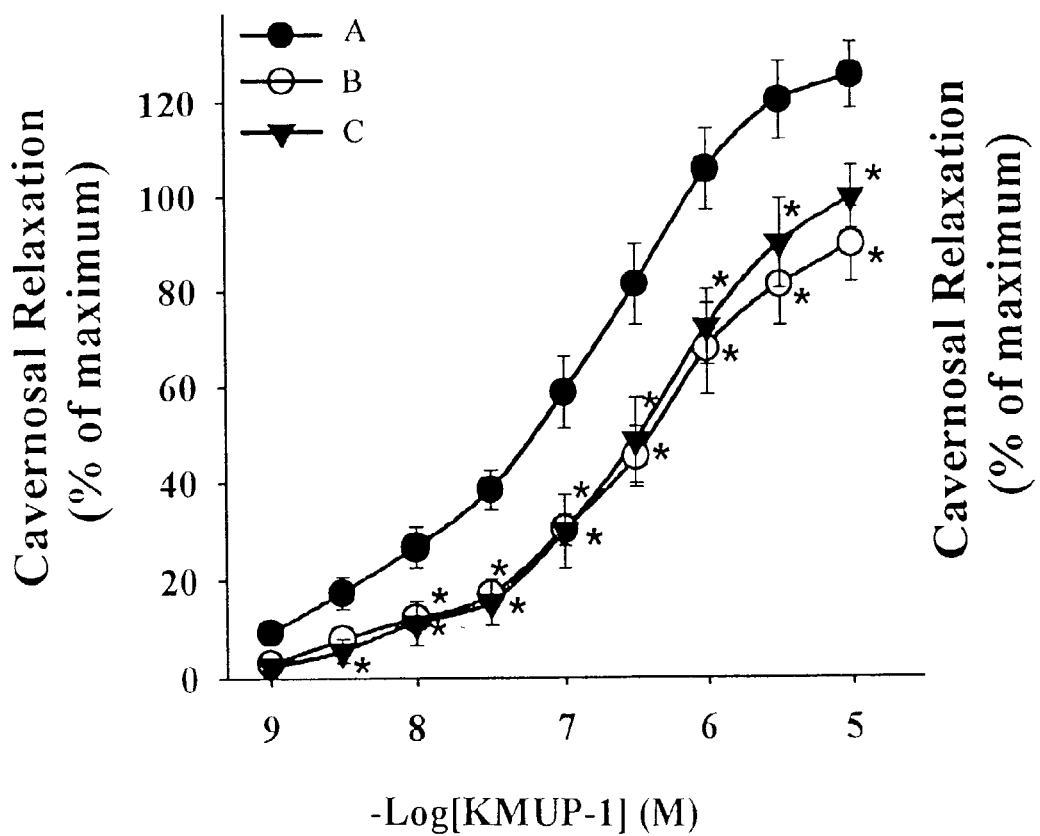

FIG. 5 Effects of KMUP-1 (A) and sildenafil (B) on phenylephrine-precontracted rabbit corpus cavernosum in the absence and presence of L-NAME, ODQ FIG. 5(A) Effects of KMUP-1 on phenylephrine (10 $\mu$M)-precontracted rabbit corpus cavernosum in the absence and presence of L-NAME (100 $\mu$M), ODQ (1 $\mu$M). *P<0.05, n=12 as compared with the KMUP-1 (two way repeated measures ANOVA followed by Student-Newman-Keuls test).

Figure 5B:
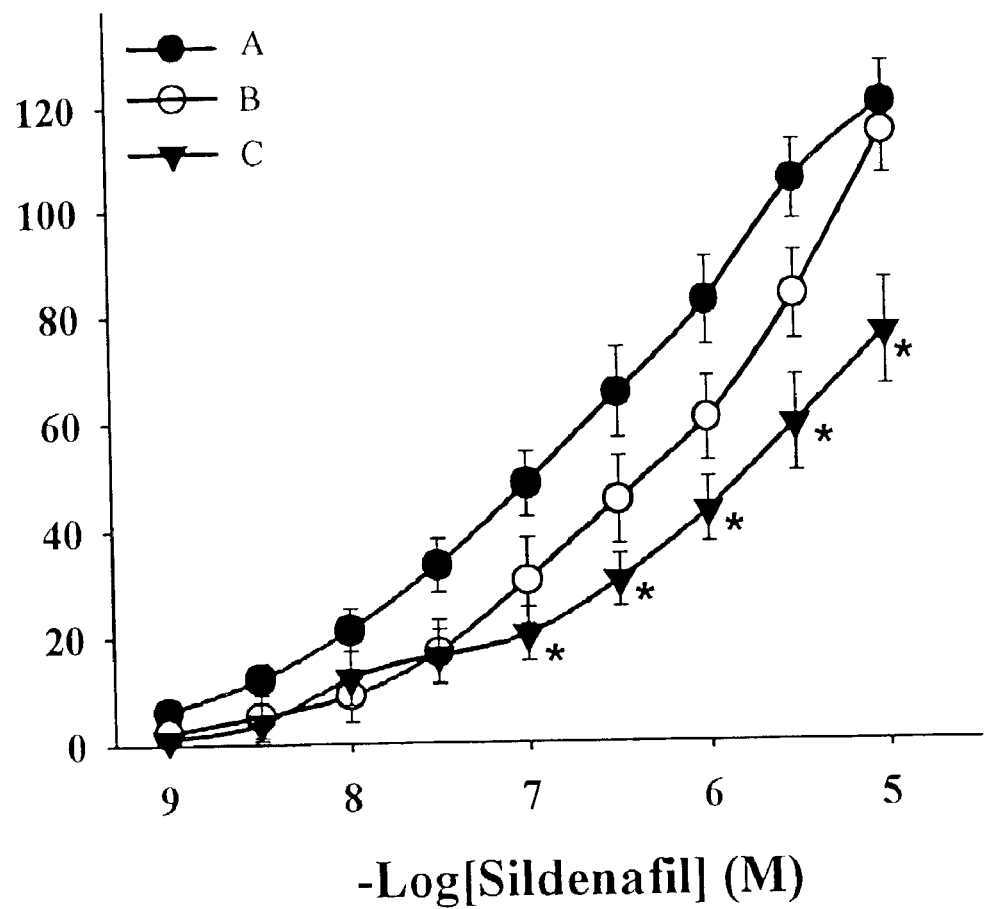

FIG. 5(B) Effects of sildenafil on phenylephrine (10 $\mu$M)-precontracted rabbit corpus cavernosum in the absence and presence of L-NAME (100 $\mu$M), ODQ (1 $\mu$M). *P<0.05, n=12 as compared with the KMUP-1 (two way repeated measures ANOVA followed by Student-Newman-Keuls test).
   A . . . control
   B . . . after L-NAME (100 $\mu$M)
   C . . . after ODQ(1 $\mu$M)

Figure 6:
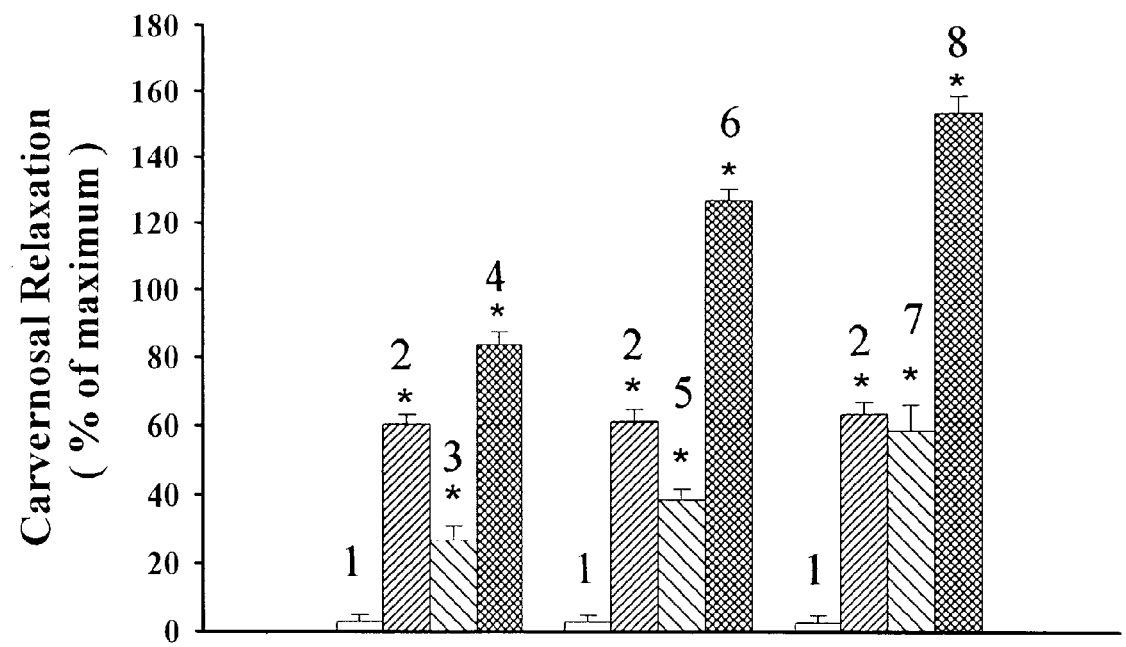
Figure 6:
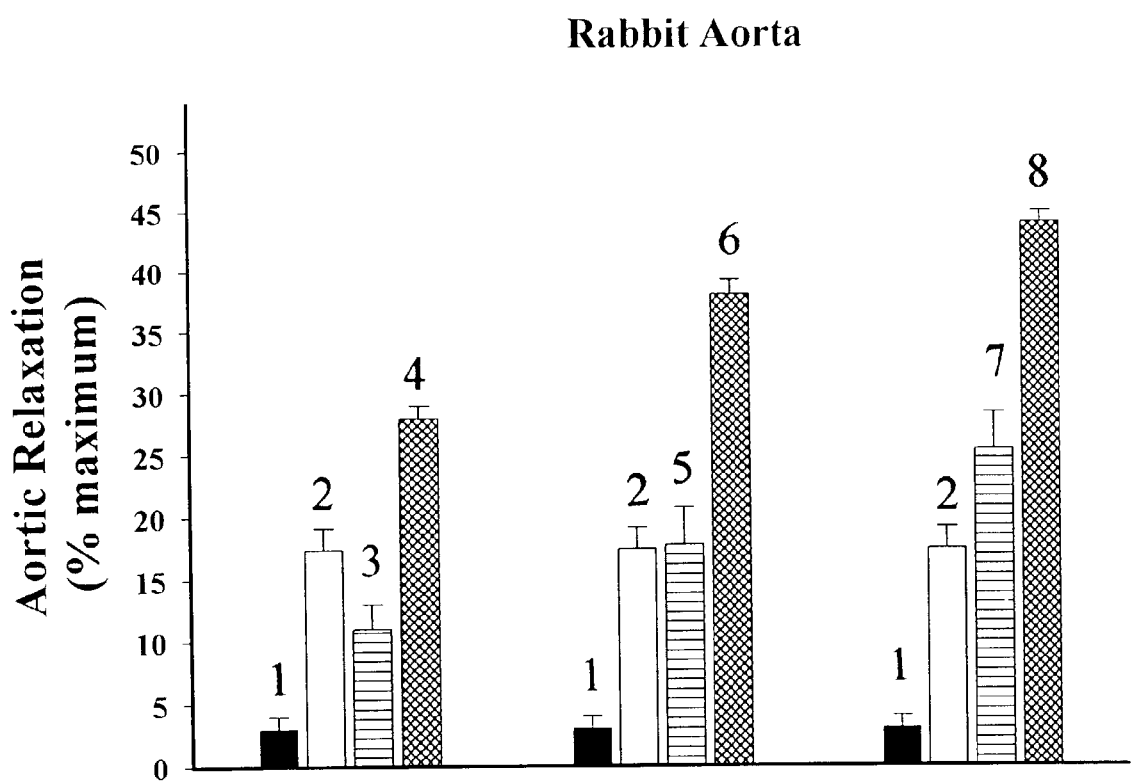
Figure 6:
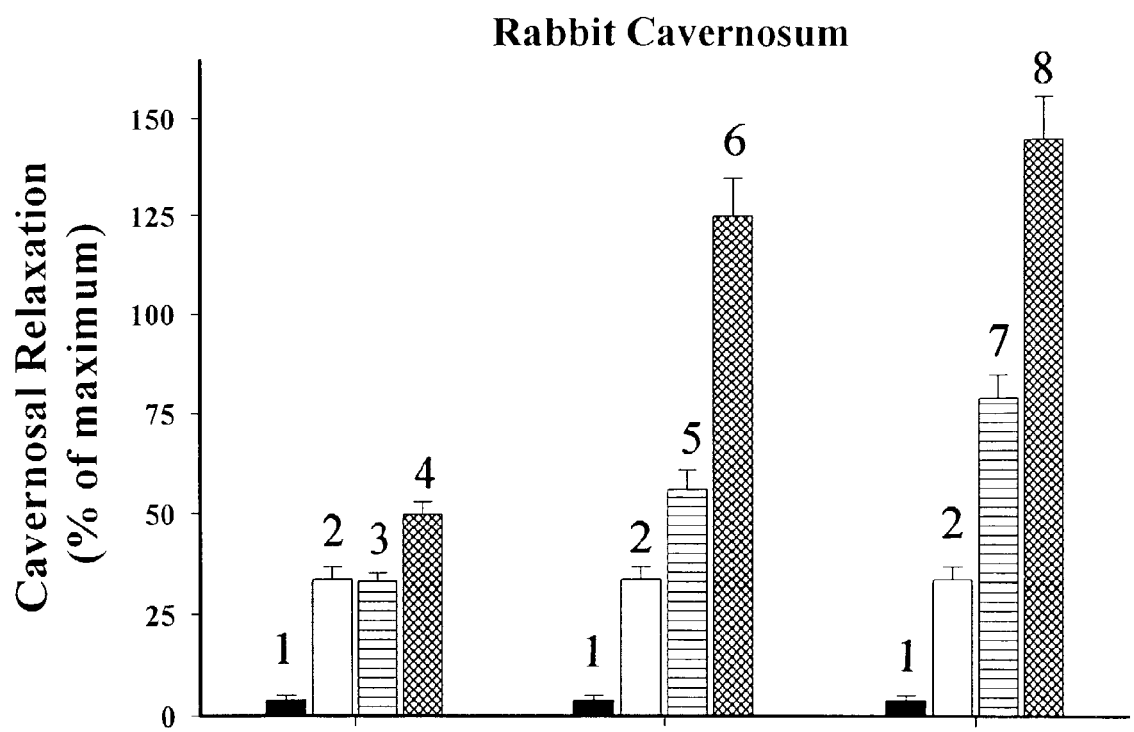

FIG. 6 Additive effects of KMUP-1, KMUP-2 and IBMX on phenylephrine-precontracted rabbit carvernosal strips. Each value represents the mean ±S.E., *P<0.05, n=8 as compared with the control value. (ANOVA followed by Dunnett's test).control:solvent control.

FIG. 6(A) Additive effects of KMUP-1, KMUP-2 and IBMX on phenylephrine-precontracted rabbit carvernosal strips. Each value represents the mean ±S.E., *P<0.05, n=8 as compared with the control value. (ANOVA followed by Dunnett's test).control:solvent control.
   1 . . . Vehicle
   2 . . . IBMX (0.5 $\mu$M).
   3 . . . KMUP-1 (0.01 $\mu$M).
   4 . . . IBMX (0.5 $\mu$M)+KMUP-1 (0.01 $\mu$M)
   5 . . . KMUP-2 (0.05 $\mu$M).
   6 . . . IBMX (0.5 $\mu$M)+KMUP-1 (0.05 $\mu$M)
   7 . . . KMUP-2 (0.1 $\mu$M).
   8 . . . IBMX (0.5 $\mu$M)+KMUP-1 (0.1 $\mu$M)

FIG. 6(B). Additive effects of KMUP-2 (0.01, 0.05, 0.1 $\mu$M) and IBMX (0.5 mM) on phenylephrine (10 mM)-precontracted rabbit aortic rings.

FIG. 6(C). Additive effects of KMUP-2 (0.01, 0.05, 0.1 mM) and IBMX (0.5 mM) on phenylephrine (10 mM)-precontracted corpus cavernosum. Each value represent the mean ±S.E., *P<0.05, n=8 as compared with the control value (ANOVA followed by Dunnett's test).
   1 . . . Vehicle
   2 . . . IBMX (0.5 $\mu$M).
   3 . . . KMUP-2 (0.01 $\mu$M).
   4 . . . IBMX (0.5 $\mu$M)+KMUP-2 (0.01 $\mu$M)
   5 . . . KMUP-2 (0.05 $\mu$M)
   6 . . . IBMX (0.5 $\mu$M)+KMUP-2 (0.05 $\mu$M)
   7 . . . KMUP-2 (0.1 $\mu$M).
   8 . . . IBMX (0.5 M)+KMUP-2 (0.1 $\mu$M)

FIG. 7 Effects of KMUP-1, KMUP-2 and sildenafil on guanosine 3',5'-cyclic monophosphate levels in rabbit corpus cavernosum smooth muscle cells. Each value represents the mean+s.e. from three independent experiments. *P50.05 as compared with the control (ANOVA followed by Dunnett's test). CTL: solvent control.
   1 . . . KMUP-1
   2 . . . sildenafil
   3 . . . KMUP-2

Figure 7A:
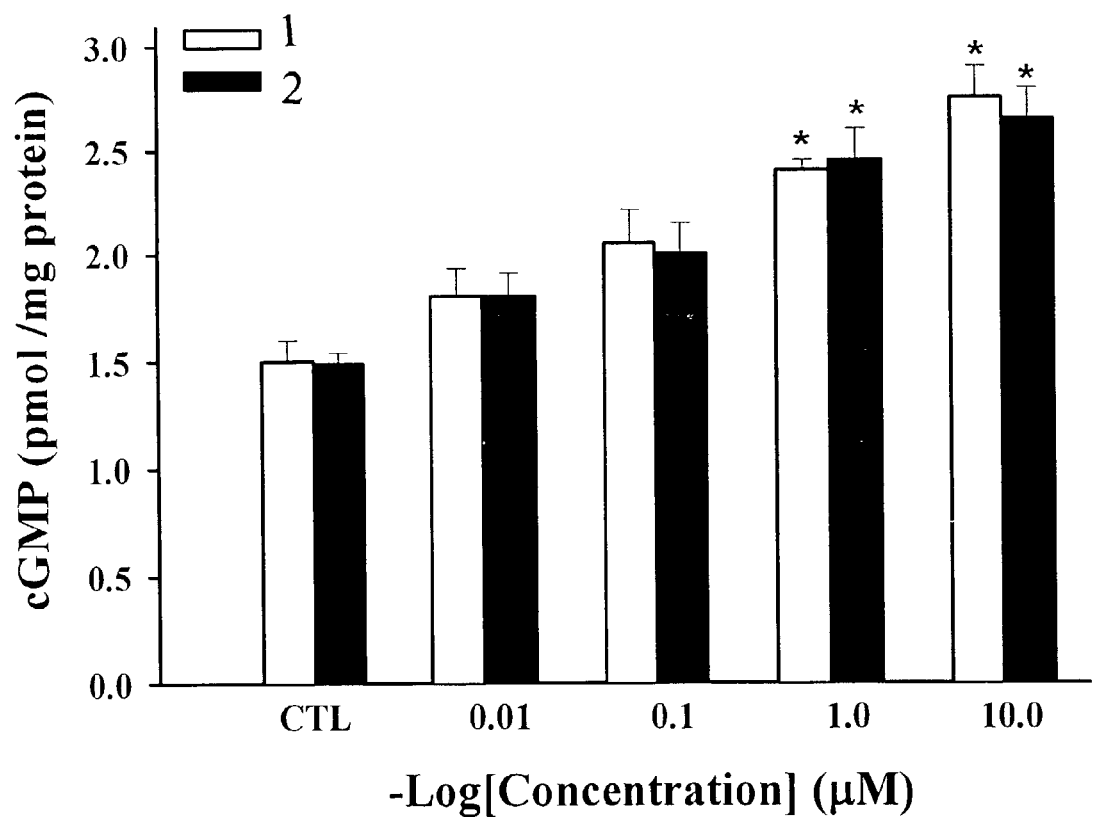

FIG. 7(A) Effects of KMUP-1 (0.01, 0.1, 1, 10 m M) and sildenafil (0.01, 0.1, 1, 10 m M) on guanosine 3',5'-cyclic monophosphate levels in rabbit corpus cavernosum smooth muscle cells.

Figure 7B:
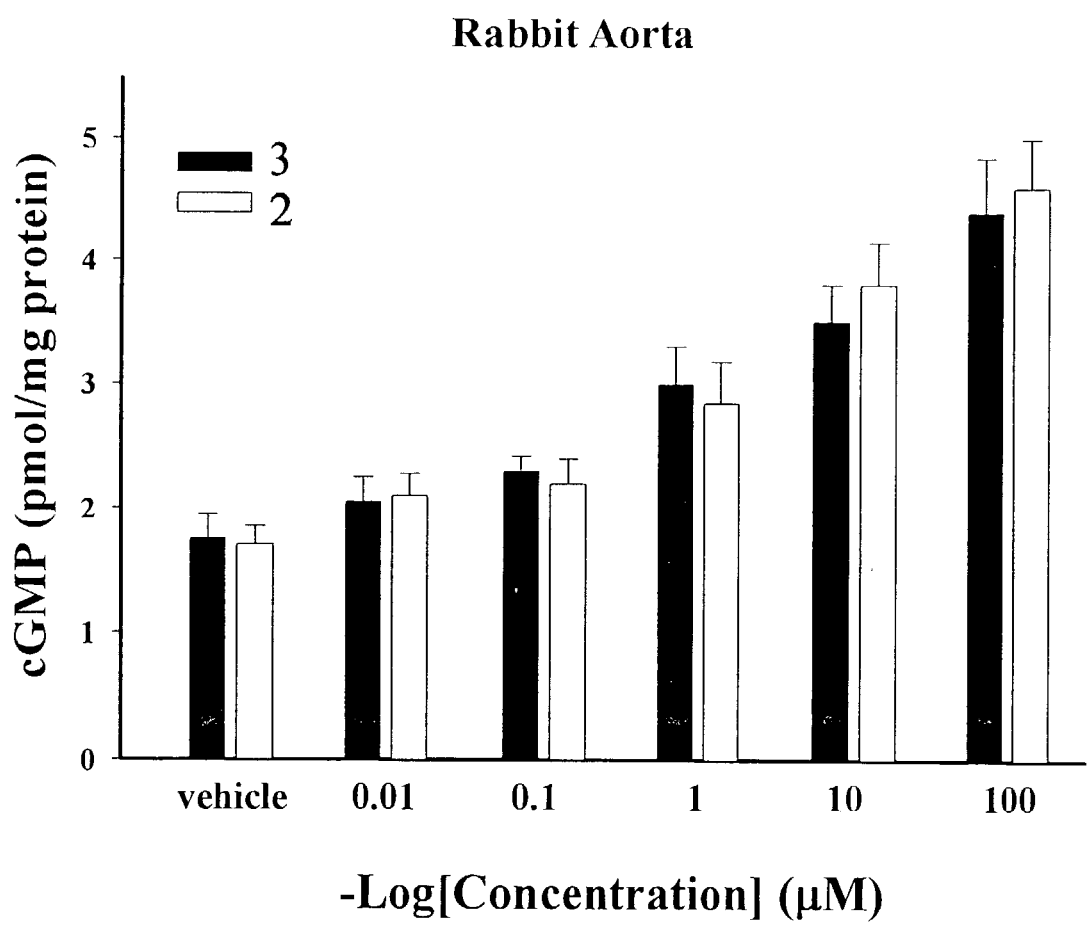

FIG. 7(B). Effects of KMUP-2 (0.1, 1, 10, 100 mM) and sildenafil (0.1, 1, 10, 100 mM) on guanosine 3',5'-cyclic monophosphate levels in rabbit aorta smooth muscle cells.

Figure 7C:
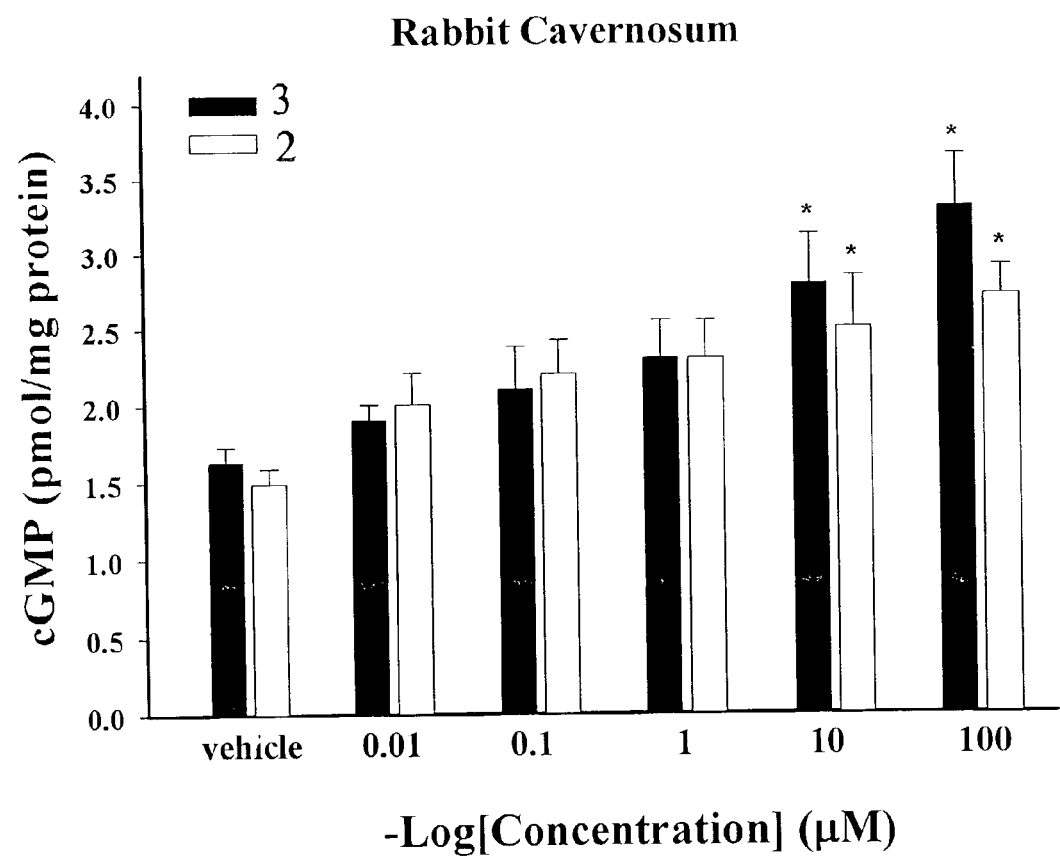

FIG. 7(C). Effects of KMUP-2 (0.1, 1, 10, 100 mM) and sildenafil (0.1, 1, 10, 100 mM) on guanosine 3',5'-cyclic monophosphate levels in rabbit corpus cavernosum smooth muscle cells.

Figure 8A:
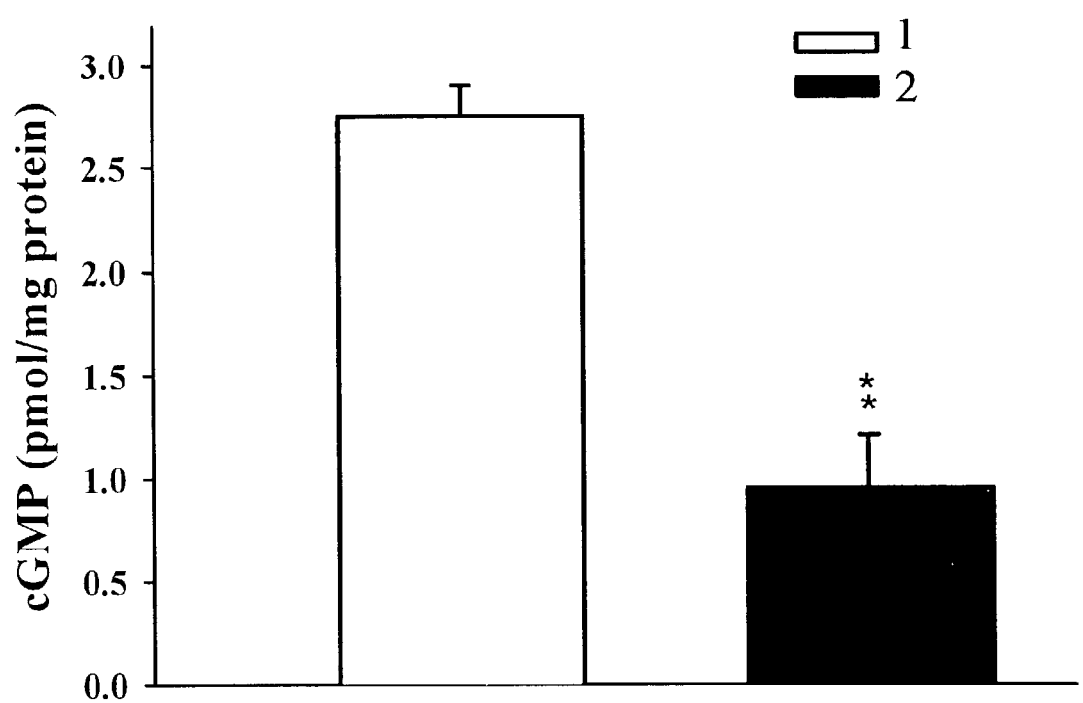

FIG. 8 Effects of KMUP-1, KMUP-2 on guanosine 3',5'-cyclic monophosphate levels in rabbit corpus cavernosal smooth muscle cells and in the absence or presence of ODQ (10 μM) and methylene blue (100 μM). Each value represents the mean ±S.E., FIG. 8(A) Effects of KMUP-1 (10 μM) on guanosine 3',5'-cyclic monophosphate levels in rabbit corpus cavernosal smooth muscle cells and in the absence or presence of ODQ (10 μM) and methylene blue (100 μM). Each value represents the mean ±S.E., from 3 independent experiments. **P<0.01 as compared with the KMUP-1 (ANOVA followed by Dunnett's test).

1 . . . KMUP-1
2 . . . after ODQ

Figure 8B:
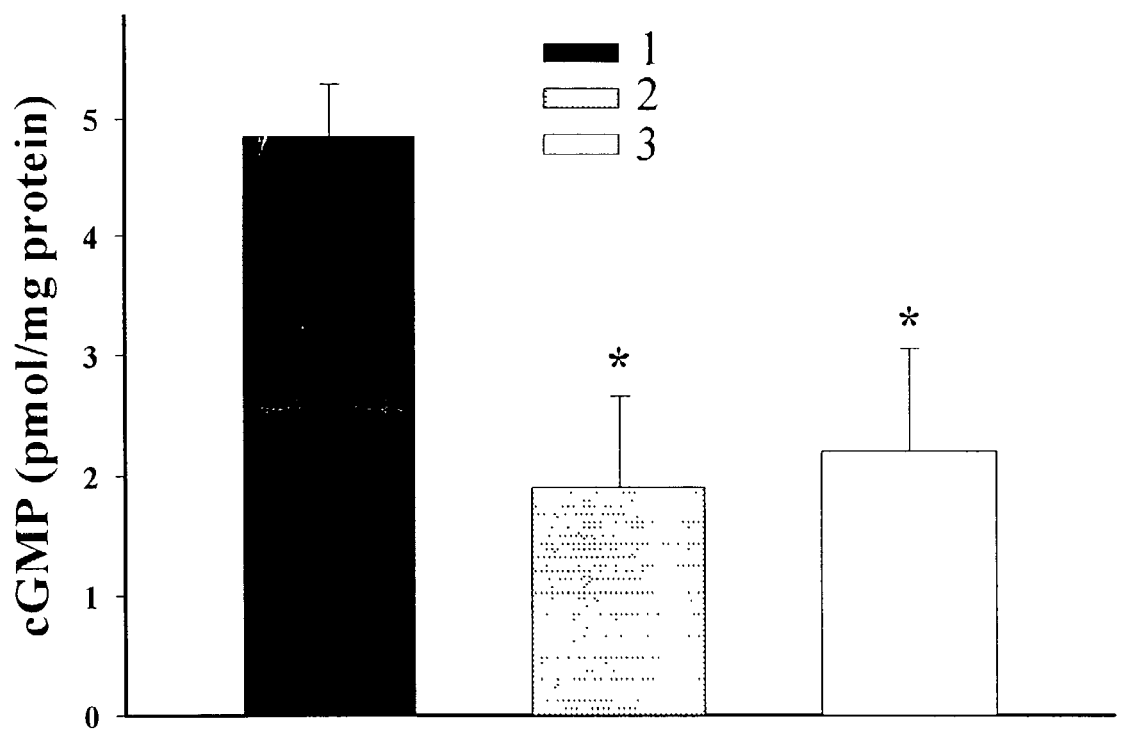

FIG. 8(B). Effects of KMUP-2 on guanosine 3',5'-cyclic monophosphate levels in rabbit aorta smooth muscle cells in the absence or presence of ODQ (10 mM) and methylene blue (100 mM).

1 . . . KMUP-2
2 . . . after methylene blue
3 . . . after ODQ

Figure 8C:
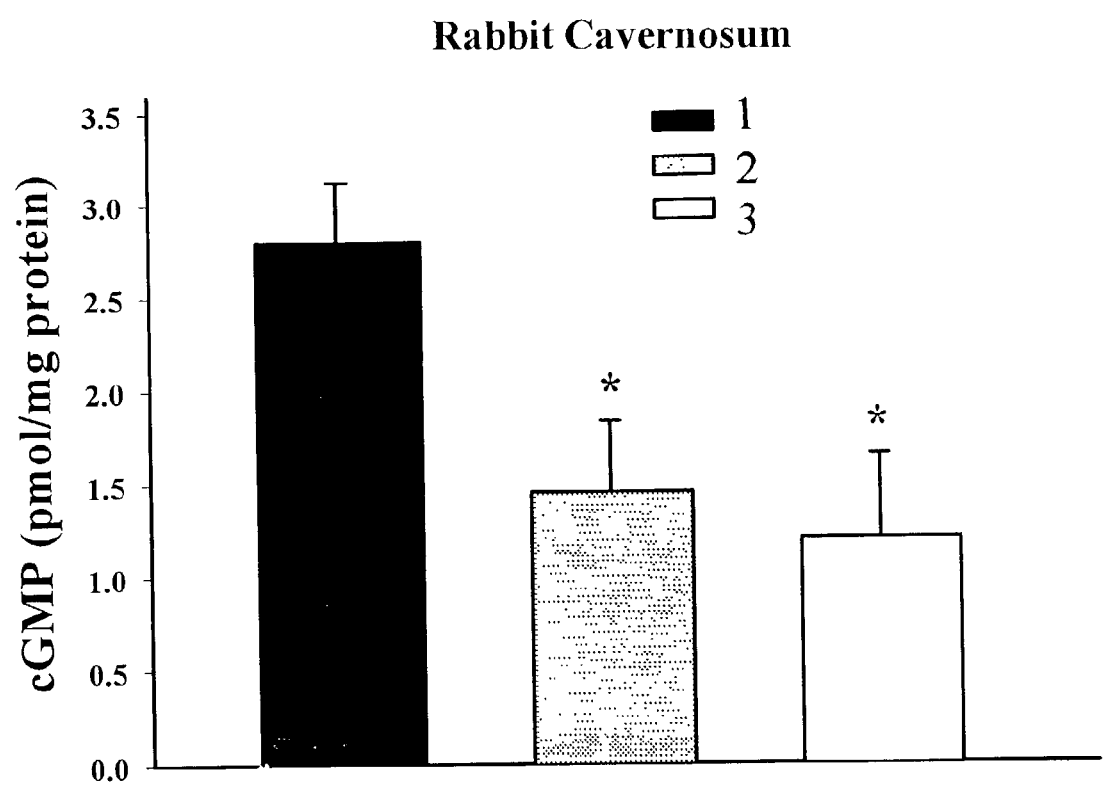

FIG. 8(C). Effects of KMUP-2 on guanosine 3',5'-cyclic monophosphate levels in corpus cavernosum smooth muscle cells and in the absence or presence of ODQ(10 mM) and methylene blue (100 mM).

1 . . . KMUP-2
2 . . . after methylene blue
3 . . . after ODQ

DETAILED DESCRIPTION OF THE INVENTION

The invention disclosed serial theophylline (1-methyl, 3-methylxanthine) and 1-methyl, 3-isobutyl xanthine (IBMX) derivatives chemically with formula I and II

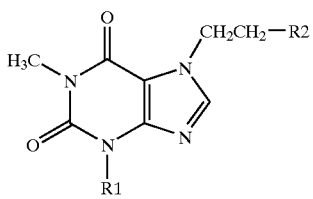

[I]

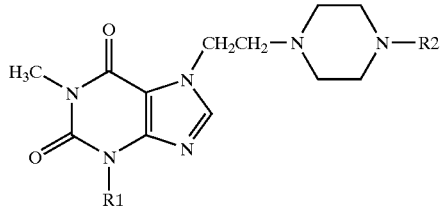

[II]

$R_1$ is present —$CH_3$ or —$CH_2CH (CH_3)_2$; $R_2$ selected from the group of

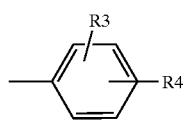

$R_3$ and $R_4$ selected from the group of $OCH_3$, $CH_3$, halogen, and $NO_2$, the halogen is present F, Cl, Br, I.

The nonadrenergic/noncholinergic neurotransmitter NO (nitric oxide) plays a crucial role in attenuating smooth muscle contraction, inducing smooth muscle relaxation, and penile erection. Several vasoactive agents, including NO and PDE (phosphodiesterase) inhibitors, initiate and/or enhance CCSM (corpus cavernosum smooth muscle) relaxation (Soderling S. H. et al., Curr. Opin. Cell Biol., 12, 174–179, 2000). Soluble guanylyl cyclase, when activated by $NO_2$ catalyzes the formation of cGMP from GTP, whereas cGNP-specific phosphodiesterases (PDEs) catalyze the hydrolysis of cGMP to GMP. Termination of signal transduction by hydrolysis of cGMP (guanosine 3',5'-cyclic monophosphate) depends on the specificity and expression of PDE (phosphodiesterase) isozymes in the target tissues (Juilfs et al., 1999). One such class of drugs is sildenafil, an inhibitor of cyclic GMP-specific PDE, for use in male erectile dysfunction (Wallis R. M. et al., Am. J. Cardiol., 83, 3C–12C, 1999).

The physiologic regulation of penile tumescence involves a balance between relaxant and contractile events. Relaxation is mainly promoted by endothelium-dependent mechanisms and stimulation of nitrergic nerves. In contrast, the adrenergic neuro-transmission has been reported as a promoter of penile flaccidity through the activation of alpha-adrenergic receptors (Angulo J. et al., Urology., 57, 585–589, 2001).

We must emphasize KMUP compound that have described on this invention, including KMUP-1 and KMUP-2, are classified into derivatives of theophylline-based compounds. The said KMUP-1 and KMUP-2 that are theophylline-based derivative shown on FIG. 1, the chemical name of KMUP-1 is 7-[2-[4-(2-chlorophenyl)piperazinyl]-ethyl]-1,3-dimethylxanthine), KMUP-2 is 7-[2-[4-(2-methoxyphenyl)piperazinyl]-ethyl]-1,3-dimethylxanthine). The derivatives of theophylline-based compounds, for example shown as formula I and II, whether $R_1$ is present —$CH_3$ or —$CH_2CH(CH_3)_2$; $R_2$ selected from the group

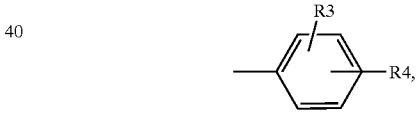

$R_3$ and $R_4$ selected from the group of $OCH_3$, halogen, and $NO_2$, the halogen is present F, Cl, Br, I.

General synthesis of theophylline-based analogues, first obtain compounds A and B through the following step. Second dissolved compound A or B in methanol, according to targeting products required, was added with suitable reagent can obtain derived compound of theophylline. Dissolve theophylline (1,3-dimethylxanthine) into dibromoethane in a glass reacter, followed by boiling and mixing at 100° C. on mantle heater and refluxed for 4 hours, equipped with a cooling condenser to return the vaporized solvent. Till solid completely melt, then added with NaOH as catalyst to react under 100° C. and boiling for overnight, leading white solid precipitated and NaBr soluble in upper water layer. The white solid precipitate was filtered, dissolved in methanol, concentrated under reduced pressure to obtain white coarse crystal, and then recrystallized with methanol to obtain the pure white crystal compound A (N7-bromoethyl theophylline).

Dissolve 3-isobutyl-1-methylxanthine (IBMX) into dibromoethane in a glass reacter, followed by boiling and mixing at 100° C. on mantle heater and refluxed for 4 hours, equipped with a cooling condenser to return the vaporized solvent. Till solid completely melt, then added with NaOH as catalyst to react under 100° C. and boiling for overnight, leading white solid precipitated and NaBr soluble in upper water layer. The white solid precipitate was filtered, dissolved in methanol, concentrated under reduced pressure to obtain white coarse crystal, and then recrystallized with methanol to obtain the pure white crystal compound B (N7-bromoethyl IBMX).

Compound A dissolved in methanol, according to targeting products required, was added with 1-(2-Chlorophenyl) piperazine, 1-(m-Chlorophenyl) piperazine, 1-(4-Nitrophenyl) piperazine, and 1-(o-Metyhoxyphenyl) piperazine, respectively, to processes the amination with piperazine moiety, using NaOH as catalyst, and reflux for 4 hours in methanol to precipitate, to dissolve the solid product, and to recrystallize with methanol to obtain theophylline-based or IBMX-based compounds (omitted), such as following:

Compound 1: N7-{2-[4(2-chlorophenyl)piperazinyl]ethyl}, 1,3-methyl xanthine.
Compound 2: N7-{2-[4(3-chlorophenyl)piperazinyl]ethyl}, 1,3-methyl xanthine
Compound 3: N7-{2-[4-(2-nitrophenyl)piperazinyl]ethyl}, 1,3-methyl xanthine.
Compound 4: N7-{2-[4-(4-nitrophenyl)piperazinyl]ethyl}, 1,3-methyl xanthine.
Compound 4: N7-{2-[4(4-chlorophenyl)piperazinyl]ethyl}, 1,3-methyl xanthine
Compound 6: N7-{2-[4-(2-nitrophenyl)piperazinyl]ethyl}, 1,3-methyl xanthine.
Compound 7: N7-{2-[4(2-chlorophenyl)piperazinyl]ethyl}, 3-isobutyl-1-methyl xanthine.
Compound 8: N7-{2-[4(2-methoxyphenyl)piperazinyl]ethyl}, 1,3-methylxanthine.

Reaction of compound-B and above piperazine derivative is able to obtain similar results, in which 1,3-methyl xanthine is substituted with 1-methyl, 3-isobutyl xanthine.

Here, we observed that KMUP-1 and KMUP-2 (KMUPs) possesse concentration-dependent relaxant activities in rabbit CCSMs. KMUP-1 and KMUP-2 produced rabbit CCSM (corpus cavernosum smooth muscle) relaxations in both endothelium-intact and deprived muscles. This relaxation of KMUPs were reduced by removing endothelium from CCSMs. Guanethidire and atropine treatment had no significant effects on KMUPs-induced relaxations. These results suggest that KMUPs-caused relaxation is un-associated with adrenergic and cholinergic neuronal function. The relaxant effect of KMUPs on endothelium deprived and NOS (nitric oxide synthase) inhibitor-pretreated CCSMs still exist. These facts indicated that KMUPs might have NO-independent relaxant effects on CCSMs. NO (nitric oxide) has been shown to be the major endothelium derived relaxing factor (EDRF) in the penile CCSM (corpus cavernosum smooth muscle) (Kim N. et al., *J. Clin. Invest.*, 88, 112–118, 1991). Relaxation of CCSMs appears to occur via NO-elicited activation of gunylate cyclase and cGMP formation (Christ G. J. et al., *J. Androl.*, 14, 319–328, 1993). The CCSM relaxant effects of KMUP-1 was significantly blunted but not inhibited by pretreatment with sGC inhibitors and the NOS inhibitor. We suggest that other mechanisms of relaxation are activated in addition to the stimulation of NO/sGC/cGMP pathway.

In this invention, we observed that the combination of KMUP-1/KMUP-2 (KMUPs) and IBMX have an additive effect on CCSMs relaxations. Recently, we have demonstrated that KMUP-1 affected cGMP breakdown at 100 μM, due to it inhibited the enzyme activity of PDE in human platelets. Furthermore, KMUP-1 significantly raised the intracellular cGMP levels in concentration-dependent manners in primary rabbit CCSM cells. These results further confirm that KMUP-1 activate the NO/sGC/cGMP pathway and inhibit the phosphodiesterase (PDE) or cGMP breakdown, and therefore elevate the intracellular cGMP levels leading to the CCSM relaxation as previously in smooth muscle (Wu B. N. et al., *Br. J. Pharmacol.*, 134, 265–274, 2001). $K^+$ channel opener reduces the tissue tension or contractile force in response to stimulation of the CCSM (Anderson. K. E. *Pharmacol. Rev.*, 45, 253–308, 1993). Vasodilators depend on the $K^+$ channel mechanism lose their effects when exposed to high $K^+$ solutions, because an increase in extracellular $K^+$ attenuates the $K^+$ gradient across the plasma membrane, thus rendering the $K^+$ channel-activating mechanism ineffective (Khan S. A. et al., *J. Pharmacol. Exp. Ther.*, 284, 838–846, 1998). $K^+$ channels can regulate corporeal smooth muscle tone, and also play a significant role in corporeal smooth muscle tone (Christ G. J. et al., *J. Androl.*, 14, 319–328, 1993). These authors further suggested that impairment in $K^+$ channels activity may contribute to erectile dysfunction. Thus, the possibility of $K^+$ channels activaticn by KMUP-1 was further investigated. The importance of $K^+$ channel-mediated hyperpolarization of KMUP-1 was provided by the differential potency of KMUP-1 in relaxing PE-induced versus KCl-induced contractions. KMUP-1 produced relaxation in this way, since its effect was almost completely blunted in high $K^+$ (60 mM) condition. In these situations, KMUP-1-induced increase in $K^+$ efflux would not hyperpolarize CCSMs (corpus cavernosum smooth muscles) sufficiently to inhibit transmembrane $Ca^{2+}$ influx as in aortic smooth muscle (Wu B. N. et al., *Br. J. Pharmacol.*, 134, 265–274, 2001). Relaxant effects of KMUP-1, reduced by a $K^+$ channel blocker TEA (Tetraethylammonium), a $K_{ATP}$ channel blocker glibenclamide (Lee S. W. et al., *Int. J. Impot. Res.*, 11, 179–188, 1999), a voltage-dependent $K^+$ channel blocker 4-AP (aminopyridine) (Sobey C. G. et al., *Br. J. Pharmacol.*, 126, 1437–1443, 1999) and $Ca^{2+}$-dependent $K^+$ channel blockers apamin (Nakagawa A. et al., *J. Cardiovasc. Pharmacol.*, 14, 38–45. 1989) and ChTX (Charybdotoxin) (Garcia M. L. et al., *Am. J. Physiol.*, 269, C1–C10, 1995) further suggest the relaxant effect of KMUP and theophylline-based derivative might be partly associated with $K^+$ channel activities.

In the present study, intracavernous injection of KMUPs dose-dependently resulted in rises of ICP, without significant change in blood pressure. Our KMUP and theophylline-based derivative displayed similar duration of tumescence as sildenafil. The results presented here provide the evidence as previously (Wu B. N. et al., *Br. J. Pharmacol.*, 134, 265–274, 2001) that the CCSM relaxant activities of KMUP-1 are mediated via inhibition of PDE (phosphodiesterase) and associated cGMP metabolism, $K^+$ channels activity, and activation of NO/sGC/cGMP pathway. As obtained accumulation of cGMP may further enhance the $K^+$ efflux, leading to blunt of $Ca^{2+}$ influx-associated contractility in CCSMs. Combination of these multiple pathways may thus attribute to significant relaxation of CCSMs and associated penile erection. Here, it is suggested that NO-releasing, sGC activation, PDE (phosphodiesterase) inhibition and associated cGMP increasing and $K^+$ channel activities of KMUP and theophylline-based derivative are the major determinants for its CCSM (corpus cavernosum smooth muscle) relaxation effects in rabbit. The in vivo results of ICP (intracavernous pressure) for sildenafil and theophylline-based derivative are consistent with the in vitro measurements of cGMP for them. These potent CCSMs relaxant and penile erection activities of theophylline-based derivative might be useful to treat erectile dysfunction.

On the other hands, we also observed that the combination of theophylline-based derivative have an additive effect to enhance learning and memory in human being. Long-term potentiation (LTP) is a potential cellular mechanism underlying learning and memory. Nitric oxide (NO) acts as a retrograde messenger and its downstream effectors are also involved in the modulation of synaptic plasticity in various brain regions such as hippocampus, amygdala, cerebellum, brain stem, cortex etc. Although nitric oxide (NO) is thought to affect synaptic potentiation in various brain regions, the NO-cGMP-PKG pathway involved in memory acquisition in living animals is still unclear. To address this question, we investigated the modulation of synaptic plasticity both in vitro and in vivo by using the novel compound KMUP and theophylline-based derivative, which greatly potentiates the response of soluble guanylate cyclase to NO. Theophylline-based derivative greatly enhanced the induction of LTP in Schaffer collateral—CA1 pathway of hippocampal slices at weak tetanus, which was markedly reduced by L-NAME, ODQ, and KT5823. The stimulating parameter which induced long-lasting depression was shifted to a lower frequency by theophylline-based derivative. Furthermore, simultaneous perfusion of theophylline-based derivatives with different concentration of NO donor induced LTP or LTD when the hippocampal slices were stimulated at a frequency as low as 0.02 Hz. The effects of theophylline-based derivative on the behavioral tasks in the following anomal models were examined: Morris water maze, passive inhibitory and active avoidance tests, and rotorod test. It was found that theophylline-based derivative greatly improved learning and memory in these behavioral tasks. KMUP-1 injected (1 mg/kg,i.p.) 10 min before the training shortened the escape latency in water maze, increased the retention scores in passive inhibitory avoidance task, decreased the retention time in active avoidance test, and enhanced the motor coorfination in the examination of rotorod. However, KMUP-1 given 30 min after foot-shock did not affect the retention of passive inhibitory avoidance. The enhancement of learning behaviors by KMUP and theophylline-based derivative were significantly antagonized by L-NAME and KT5823. YC-1 thus enhanced LTP, learning and memory in an NO-cGMP-PKG-dependent pathway and is a promising drug to enhance learning and memory in human being.

The compositions of this invention will include various excipients; carriers or diluents and pharmaceutically approved PH of processed salts in accordance to necessity to form composition with therapeutic efficacy. These pharmaceutical preparations may be in solid form for oral and rectal administration; liquid form or non-intestinal injection form; or ointment form for direct application on affected part. Such solid forms are manufactured according to common pharmaceutical preparation methods, which will include disintegrant like starch; sodium carboxymethylcellulose, adhesive like ethanol; glycerine, or magnesium stearic acid; lactose to obtain pharmaceutical preparation like tablets or filled into capsules of suppositories. Solution which include a compound of this ingredient could use buffers of phosphoric nature to adjust the PH to suitable level, before adding the adjutant; emulsifier to produce injection dose or other liquid preparation. In the present invention a compound or a pharmaceutical composition could be manufactured by mixing synthetic acid salts with various fundamental preparations to form ointments according to known pharmaceutical manufacturing methods. Pharmaceutical compositions manufactured according to this invention could be used on mammals to produce the efficacy of the main ingredient. General dosage could be adjusted according to the degree of symptoms, and normally a person will require 50 to 300 mg each time, three times per day.

PHARMACEUTICAL ACTIVITY

The pharmaceutical activity of the compounds of this invention have been proven by the following pharmaceutical experiments.

Male New Zealand white rabbits (2.5–3 kg) were provided from National Laboratory Animal Breeding and Research Center (Taipei, Taiwan) and housed under conditions of constant temperature and controlled illumination. Food and water were available ad libitum. The study was approved by the Animal Care and Use Committee of the Kaohsiung Medical University. Tetraethylammonium (TEA), 4-aminopyridine (4-AP), glibenclamide, phenylephrine, methylene blue, apamin, charybdotoxin, 1H-[1,2,4] Oxadiazolo[4,3-a]quinoxalin-1-one (ODQ), $N^w$-nitro-L-arginine methyl ester (L-NAME) and 3-isobutyl-1-methylxanthine (IBMX) were obtained from Sigma Chemical Co. (St. Louis, Mo., U.S.A.). Sildenafil citrate was supplied by the Cadila Healthcare Ltd. (Maninagar, India). All other reagents used were from E. Merck (Darmstadt, Germany). KMUP-1, synthesized in this laboratory, was dissolved in 10% absolute alcohol, 10% propylene glycol and 2% 1N HCl at 10 mM. Serial dilutions were made in distilled water.

Corpus cavernosum smooth muscle relaxant activity As shown in FIG. 2, cumulative concentrations of KMUP-1 (0.001–10 $\mu$M) produced concentration-dependent relaxations both in endothelium-denuded (EC−) and endothelium-intact (EC+) corpus cavernosum smooth muscles, indicating that KMUP-1-induced endothelium-independent relaxation. However, KMUP-1 did have a significant shift in the response curve after endothelium denudation, suggesting that at least part of the observed effect is endothelium-dependent. The estimated $EC_{50}$ value for KMUP-1 in EC+ corpus cavernosum smooth muscles was $-\log EC_{50}=7.19\pm0.09$. Additionally, KMUP-1 completely relaxed the corpus cavernosum smooth muscle strips at 10 $\mu$M.

Effects on $K^+$ channels KMUP-1 (0.001–10 $\mu$M) caused a concentration-dependent relaxation in phenylephrine-contracted corpus cavernosum smooth muscles. However, KMUP-1 had a great reduction of relaxation in the presence of high $K^+$ (60 mM) (FIG. 3). corpus cavernosum smooth muscles relaxation of KMUP-1 were inhibited by a $K^+$ channel blocker Tetraethylammonium (TEA) ($-\log EC_{50}=5.37\pm0.05$), a $K_{ATP}$ channel blocker glibenclamide ($-\log EC_{50}=6.57\pm0.15$), a voltage-dependent $K^+$ channel blocker 4-aminopyridine (4-AP) ($-\log EC_{50}=5.83\pm0.17$) and $Ca^{2+}$-dpendent $K^+$ channel blockers apamin ($-\log EC_{50}=5.85\pm0.11$) and charybdotoxin ($-\log EC_{50}=5.63\pm0.09$) (FIG. 4).

Effects on NO synthase and soluble guanylyl cyclase Pretreatment with a NOS (nitric oxide synthase) inhibitor L-NAME ($-\log EC_{50}=6.51\pm0.08$) and sGC (soluble guanylyl cyclase) inhibitors ODQ (1H-[1,2,4]Oxadiazolo[4,3-a]quinoxalin-1-one) ($-\log EC_{50}=6.79\pm0.12$), the relaxations elicited by KMUP-1 ($-\log EC_{50}=7.19\pm0.09$) were significantly inhibited (FIG. 5).

Phosphodiesterase assay. Human platelets were isolated from whole blood using 50 mM Tris-HCl containg 5 mM $MgCl_2$ (pH 7.5) and centrifuged to prepare platelet rich plasma. Washed human platelets were resuspended in 50 mM Tris-HCl containg 5 mM $MgCl_2$ (pH 7.5). Platelets were then disrupted by sonicatio, and soluble PDE preparation was obtained by ultracentrifugation 105000 g for 60 min (4° C). The enzyme (11.5 mg/10 $\mu$l) was incubated with Tris-HCl (80 $\mu$l) and 10 $\mu$M cyclic GMP substrate (final concentration 1 $\mu$M containing 0.1 $\mu$Ci [$^3$H]-cyclic GMP) was added. After 20 min at 37° C., the samples were heated to 100° C. for 2 min. Ophiophagus Hannah snake venom (10 mg/ml, 10 $\mu$l) was then added and incubated at 37 C. for 10 min to convert the 5-GMP to the unchanged nucleosides, guanosine. An ion-exchange resin (200 $\mu$l) was added to bind all uncoverted cyclic GMP. After centrifuging, the supernatant was removed for determination in a liquid scintillation counter.

Inhibition of phosphodiesterase activity

Effects of KMUP-1 on corpus cavernosum smooth muscles were investigated after inhibition of PDE (phosphodiesterase) activity by IBMX. KMUP-1 (−log $EC_{50}$=7.21±10.12) and IBMX (0.5 $\mu$M) were additively (−log $EC_{50}$=8.65±0.14) to induce relaxation (FIG. 6A). KMUP-1 (0.01, 0.05, 0.1 $\mu$M)-induced vasorelaxation (−log $EC_{50}$=7.03 0.10) had an additive effect in the presence of IBMX (0.5 $\mu$M) (−log $EC_{50}$=10.60 0.13). In further experiments, KMUP-1 inhibited the PDE activity (29±3.1%, n=3, each performed in triplicate) at 100 $\mu$M while in comparison with sildenafil (94±4.8%, n=3) (Bin-Nan Wu et al., Br J Pharmacol, 134, 265–274, 2001).

The effects of KMUP-2 on aortic rings and corpus cavernosum smooth muscle were investigated after inhibition of PDE (phosphodiesterase) activity, using IBMX, a nonselective PDE (phosphodiesterase) inhibitor. KMUP-2 (0.01, 0.05, 0.1 $\mu$M)-induced relaxation in aortic rings (−log $EC_{50}$=5.69±0.02) and in cavernosum smooth muscle (−log $EC_{50}$=7.58±0.02) had an additive effect in the presence of IBMX (0.5 $\mu$M, −log $EC_{50}$=6.61±0.12 and −log $EC_{50}$=8.37±0.03, respectively) (FIG. 6B). In further experiments, KMUP-2 inhibited the PDE (phosphodiesterase) activity (21±2.1%, n=3, each performed in triplicate) at 100 $\mu$M in comparison with sildenafil (94±4.8%, n=3) (Rong-lyh Lin et al., Drug Development Research 55, 162–172, 2002).

Guanosine 3',5'-cyclic monophosphate enhancing activity in cavernosum smooth muscle cells Effects of KMUP-1 on guanosine 3',5'-cyclic monophosphate levels were examined in primary rabbit corpus cavernosum smooth muscle cells in the presence of IBMX (100 $\mu$M). The amount of basal release of cGMP was 1.58±0.11 pmol $mg^{-1}$ $well^{-1}$ (n=3). KMUP-1 and sildenafil at 0.01–10 $\mu$M increased the cGMP levels (FIG. 7A), which were inhibited by the pretreatment with ODQ (10 $\mu$M) (FIG. 8A). And examined the effect of KMUP-2 on guanosine 3',5'-cyclic monophosphate levels in the presence of nonselective PDE (phosphodiesterase) inhibitor IBMX (100 $\mu$M) in primary cultured rabbit aorta and corpus cavernosum smooth muscle cells. The amount of basal release of cGMP in aortic and corpus cavernosum smooth muscle cells was 1.65±0.2 and 1.62±0.1 pmol/mg/well (n=3), respectively. KMUP-2 (0.1, 1.0, 10, 100 $\mu$M) significantly increased the guanosine 3',5'-cyclic monophosphate levels in a concentration-dependent manner in rabbit and corpus cavernosum smooth muscle. Sildenafil also elicited significant elevation of cGMP ac-cumulation (FIG. 7B, 7C). The cGMP levels were significantly inhibited by pretreatments with methylene blue (100 $\mu$M) and ODQ (10 $\mu$M) in both smooth muscle cells (FIG. 8B).

Increase of ICP (intracavernous pressure) To examine whether KMUP-1 was with corporeal relaxation-associated penile erection activity, we measured the intracavernous pressure of rabbits. As shown in Table 2, The basal value of intracavernous pressure recorded was 13.3±2.6 mmHg (n=6). Intracavernous injection of KMUP-1 induced tumescence as documented by a sustained increase in intracavernous pressure. During the injection periods, the SAP (systemic arterial pressure) and HR (heart rate) were unchanged (data not show). Injection of saline induced a transient rise in intracavernous pressure in a volume-dependent manner. Nevertheless, the pressure rises often returned to the resting level within 1 min and the spike-like pressure curves were different from those of KMUP-1 and sildenafil. We believed that the transient rise in intracavernous pressure was due to the volume effect of saline. Administration of KMUP-1 and sildenafil (0.2, 0.4, 0.6 mg $kg^{-1}$) induced dose-dependent elevations in intracavernous pressure. We also found tumescence of the penile shaft did not show full erection in some cases. There are no significant differences between 2 compounds in their responses to intracavernous pressure (Table 2).

Anyone who is familiar with the said technique is able to amend and/or apply the said technique partially or totally without going beyond the Invention's spirit and coverage. Thus, the protection coverage of the Invention is determined by the descriptions stated in the application of patents.

Disruption of endothelium The endothelium lining the lacunar spaces of rabbit corpus cavernosum was disrupted and/or removed by detergent treatment using a modification of a protocol for blood vessels, described elsewhere (kim N. et al., J. Clin. Invest., 88, 112–118, 1991). The intact, isolated penis was placed in a tray containing chilled physiological salt solution (PSS). A 21-guage minicatheter was inserted into each corporal body at the proximal end of the penis. A third minicatheter was inserted into the distal end, below the glans penis, where the right and left corpora communicate. While the distal and one proximal minicatheter were clamped, 3 ml of CHAPS (wt vol.$^-$) in saline was infused into the remaining proximal catheter. After a short interval (~20 s), the clamped minicatheters were opened and the preparation was washed by infusion of saline. The corpora cavernosa were then removed and tested for endothelial integrity. Of the tissues treated with CHAPS, 75% did not relax or relaxed poorly (<10% of maximal relaxation) to acetylcholine (Ach, 1 $\mu$M) were considered to be functionally denuded of endothelium.

Tissue procurement and organ bath experiments Male rabbits were killed with pentobarbital and their penises excised rapidly and cut longitudinally into equal strips to give 3–6 segments. These segments were incubated in Kerbs-bicarbontate solution (NaCl, 118 mM; $NaHCO_3$, 25 mM; KCl, 4.7 mM; $KH_2PO_4$, 1.2 mM; $MgSO_4$, 1.2 mM; glucose, 11 mM; $CaCl_2$, 2.5 mM; pH 7.3–7.4) maintained at 37° C. and aerated with 95% $O_2$ and 5% $CO_2$. Isometric tension was recorded with a force displacement transducer (UGO BASILE, Model 7004, Italy). Rabbit corpus cavernosum smooth muscles were stretched to a resting tension of 2 g and then contracted with phenylephrine (PE, 10 $\mu$M). Tissues were also treated with guanethidine (10 $\mu$M) to block contractions caused by noradrenaline, released from adrenergic neuron, and treated with atropine (1 $\mu$M) to prevent muscarinic effects caused by acetylcholine. When the stable constriction to phenylephrine was reached, concentration-response curves to KMUP-1 (0.001–10 $\mu$M) were constructed. Data were expressed as a percentage of the maximum contractile response to phenylephrine. To examine the possible action mechanisms of KMUP-1, the rabbit corpus cavernosum smooth muscles were pretreated with sGC (soluble guanylyl cyclase) inhibitors ODQ (1 $\mu$M), a NOS (nitric oxide synthase) inhibitor L-NAME (100 μM), a K⁺ channel blocker Tetraethylammonium (TEA, 10 mM), a $K_{ATP}$ channel blocker glibenclamide (1 μM), a voltage-dependent K⁺ channel blocker 4-AP (100 μM) and $Ca^{2+}$-dpendent K⁺ channel blockers apamin (1 μM) and charybdotoxin (0.1 μM) for 30 min prior to the addition of KMUP-1. To observe whether the rabbits corpus cavernosum smooth muscle relaxation of KMUP-1 are affected by a nonselective PDE (phosphodiesterase) inhibitor, we investigated the action of KMUP-1 in the presence of IBMX (0.5 μM). In another experiment, rabbit corpus cavernosum smooth muscles were preconstricted with 60 mM KCl. The KCl solution was prepared by substituting NaCl with KCl (60 mM) in an equimolar amount.

Culture of rabbit corpus cavernosum smooth muscle cells Rabbit corpus cavernosum smooth muscles were obtained as sterile surgical specimens, the tissue was washed and cut into 1 to 2 mm pieces and placed into culture dishes with Dulbecco's modified Eagle's medium (DMEM) containing 20% fetal bovine serum (FBS), penicillin (100 U ml⁻¹), streptomycin (100 U ml⁻¹) and 2 mM Glutamine. After explants attached to the culture dish, usually 1 to 2 days, DMEM (Dulbecco's modified Eagle's medium) supplement with 10% FBS, penicillin, streptomycin, and glutamine were added. Smooth muscle cells migrated out from the explants in 3–5 days. At this time, the explants were removed, and cells were allowed to achieve confluence. Cells were detached using 0.05% trypsin, 0.02% EDTA at 37° C. for 5 minutes to establish secondary cultures. Cultures were maintained for no more than 4 passages. Cellular homogeneity was further confirmed by the presence of smooth muscle specific α-myosin and α-actin immunoreactivity. Indirect immunofluorescence staining for a variety of antigens was carried out by first plating the cells on chamber slides fixing the cells in 3.7% formaldehyde-phosphate buffered saline for 10 minutes and permeabilizing the cells with phosphate buffered saline 0.1% Triton X-100. Cells were then stained with either a mouse monoclonal antibody directed against the amino terminal 10 amino acids of α-smooth muscle actin and α-myosin (Moreland R. B. et al., J Urol., 153, 826–834, 1995).

Measurement of intracellular guanosine 3',5'-cyclic monophosphate content Intracellular cGMP concentrations in rabbit corpus cavernosum smooth muscle cells were assayed as our previously described (Wu et al., 2001). In brief, cells were finally grown in 24-well plates (10⁵ cells well⁻¹). At confluence, monolayer cells were washed with PBS and then incubated with KMUP-1 and sildenafil (0.01–10 μM) in the presence of 100 μM IBMX for 10 min as described by Park K.et al. (Biochem Biophys Res Commun., 249, 612–617, 1998). Incubation was terminated by the addition of 6% trichloroacetic acid (TCA). Cell suspensions were sonicated and then centrifuged at 2500 g for 15 min at 4° C. Then, the supernatants were lyophilized and cGMP of each sample was determined using a commercially available radioimmunoassay kits (Amersham Pharmacia Biotech, Buckinghamshire, England).

Measurement of intracavernous pressure Male rabbits were used for the investigation. After sedation with an intramuscular injection of ketamine (10 mg kg⁻¹), the rabbits were anaesthetized with intraperitoneal pentobarbital (30 mg kg⁻¹) and maintained with 10 mg kg⁻¹ if needed. The animals breathed spontaneously. The rabbits were then placed in the supine position, and the body temperature was maintained at 37° C. The femoral artery was cannulated for continuous monitoring of systemic arterial pressure (SAP) and heart rate (HR) via a pressure transducer (Spectramed, Model P10EZ, U.S.A.). Under sterile conditions, the skin overlying the penis was incised and the corpora cavernosum was exposed at the root of the penis. A 25-gunge needle was inserted into the corpus cavernosum smooth muscles for pressure recording. The needle was connected to a three-way stopcock, thus permitting the intracavernous injection of the drugs. The tube was filled with heparinized saline (50 IU 2 h⁻¹) to prevent clotting.

Intracavernous injection In 48 rabbits, divided into 2 groups, 8 animals in each group for one dose, KMUP-1 and sildenafil (0.2, 0.4, 0.6 mg kg⁻¹) were, respectively, injected into corpus cavernosum smooth muscles in a volume of less than 0.2 ml. Normal saline in increasing volumes (0.05, 0.1, 0.2 ml) was injected in four rabbits as a control group. The effects of KMUP-1 and normal saline on the intracavernous pressure (ICP) and on the duration of action were evaluated. In order to minimize the effect of the previous drug, the cavernous body was flushed with 0.2 ml normal saline before each injection and the time interval between each injection was at least 1.5 h.

Statistical evaluation of data The results are expressed as mean ±s.e.mean. Statistical differences were determined by independent and paired Student's t-test in unpaired and paired samples, respectively. Whenever a control group was compared with more than one treated group, the one way ANOVA or two way repeated measures ANOVA was used. When the ANOVA manifested a statistical difference, the Dunnett's or Student-Newman-Keuls test was applied. The P value less than 0.05 was considered to be significant in all experiments. Analysis of the data and plotting of the figures were done with the aid of software (SigmaStat and Sigma-Plot, Version 5.0, San Rafael, Calif., U.S.A.) run on an IBM compatible computer.

Disruption of endothelium The endothelium lining the lacunar spaces of rabbit corpus cavernosum was disrupted and/or removed by detergent treatment using a modification of a protocol for blood vessels, described elsewhere (kim et al., 1991). The intact, isolated penis was placed in a tray containing chilled physiological salt solution (PSS). A 21-guage minicatheter was inserted into each corporal body at the proximal end of the penis. A third minicatheter was inserted into the distal end, below the glans penis, where the right and left corpora communicate. While the distal and one proximal minicatheter were clamped, 3 ml of CHAPS (wt vol.⁻¹) in saline was infused into the remaining proximal catheter. After a short interval (~20 s), the clamped mini-catheters were opened and the preparation was washed by infusion of saline. The corpora cavernosa were then removed and tested for endothelial integrity. Of the tissues treated with CHAPS, 75% did not relax or relaxed poorly (<10% of maximal relaxation) to acetylcholine (Ach, 1 μM) were considered to be functionally denuded of endothelium.

Tissue procurement and organ bath experiments Male rabbits were killed with pentobarbital and their penises excised rapidly and cut longitudinally into equal strips to give 3–6 segments. These segments were incubated in Kerbs-bicarbontate solution (NaCl, 118 mM; $NaHCO_3$, 25 mM; KCl, 4.7 mM; $KH_2PO_4$, 1.2 mM; $MgSO_4$, 1.2 mM; glucose, 11 mM; $CaCl_2$, 2.5 mM; pH 7.3–7.4) maintained at 37° C. and aerated with 95% $O_2$ and 5% $CO_2$. Isometric tension was recorded with a force displacement transducer (UGO BASILE, Model 7004, Italy). Rabbit CCSMs were stretched to a resting tension of 2 g and then contracted with phenylephrine (PE, 10 μM). Tissues were also treated with guanethidine (10 μM) to block contractions caused by noradrenaline, released from adrenergic neuron, and treated with atropine (1 μM) to prevent muscarinic effects caused by acetylcholine. When the stable constriction to PE was reached, concentration-response curves to KMUP-1 (0.001–10 μM) were constructed. Data were expressed as a percentage of the maximum contractile response to PE. To examine the possible action mechanisms of KMUP-1, the rabbit CCSMs were pretreated with sGC inhibitors ODQ (1 μM), a NOS inhibitor L-NAME (100 μM), a $K^+$ channel blocker TEA (10 mM), a KATP channel blocker glibenclamide (1 μM), a voltage-dependent $K^+$ channel blocker 4-AP (100 μM) and $Ca^{2+}$-dpendent $K^+$ channel blockers apamin (1 μM) and charybdotoxin (0.1 μM) for 30 min prior to the addition of KMUP-1. To observe whether the rabbits CCSM relaxation of KMUP-1 are affected by a nonselective PDE inhibitor, we investigated the action of KMUP-1 in the presence of IBMX (0.5 μM). In another experiment, rabbit CCSMs were preconstricted with 60 mM KCl. The KCl solution was prepared by substituting NaCl with KCl (60 mM) in an equimolar amount.

Culture of rabbit corpus cavernosum smooth muscle cells Rabbit CCSMs (corpus cavernosum smooth muscles) were obtained as sterile surgical specimens, the tissue was washed and cut into 1 to 2 mm pieces and placed into culture dishes with Dulbecco's modified Eagle's medium (DMEM) containing 20% fetal bovine serum (FBS), penicillin (100 U $ml^{-1}$), streptomycin (100 U $ml^{-1}$) and 2 mM Glutamine. After explants attached to the culture dish, usually 1 to 2 days, DMEM supplement with 10% FBS, penicillin, streptomycin, and glutamine were added. Smooth muscle cells migrated out from the explants in 3–5 days. At this time, the explants were removed, and cells were allowed to achieve confluence. Cells were detached using 0.05% trypsin, 0.02% EDTA at 37° C. for 5 minutes to establish secondary cultures. Cultures were maintained for no more than 4 passages. Cellular homogeneity was further confirmed by the presence of smooth muscle specific α-myosin and α-actin immunoreactivity. Indirect immunofluorescence staining for a variety of antigens was carried out by first plating the cells on chamber slides fixing the cells in 3.7% formaldehyde-phosphate buffered saline for 10 minutes and permeabilizing the cells with phosphate buffered saline 0.1% Triton X-100. Cells were then stained with either a mouse monoclonal antibody directed against the amino terminal 10 amino acids of α-smooth muscle actin and α-myosin (Moreland et al., 1995).

Measurement of intracellular cyclic GMP content Intracellular cGMP concentrations in rabbit CCSM cells were assayed as our previously described (Wu et al., 2001). In brief, cells were finally grown in 24-well plates ($10^5$ cells $well^{-1}$). At confluence, monolayer cells were washed with PBS and then incubated with KMUP-1 and sildenafil (0.01–10 μM) in the presence of 100 μM IBMX for 10 min as described by Park, K.et al. (1998). Incubation was terminated by the addition of 6% trichloroacetic acid (TCA). Cell suspensions were sonicated and then centrifuged at 2500 g for 15 min at 4° C. Then, the supernatants were lyophilized and cGMP of each sample was determined using a commercially available radioimmunoassay kits (Amersham Pharmacia Biotech, Buckinghamshire, England).

Measurement of intracavernous pressure Male rabbits were used for the investigation. After sedation with an intramuscular injection of ketamine (10 mg $kg^{-1}$), the rabbits were anaesthetized with intraperitoneal pentobarbital (30 mg $kg^{-1}$) and maintained with 10 mg $kg^{-1}$ if needed. The animals breathed spontaneously. The rabbits were then placed in the supine position, and the body temperature was maintained at 37° C. The femoral artery was cannulated for continuous monitoring of systemic arterial pressure (SAP) and heart rate (HR) via a pressure transducer (Spectramed, Model P10EZ, U.S.A.). Under sterile conditions, the skin overlying the penis was incised and the corpora cavernosum was exposed at the root of the penis. A 25-gunge needle was inserted into the CCSMs for pressure recording. The needle was connected to a three-way stopcock, thus permitting the intracavernous injection of the drugs. The tube was filled with heparinized saline (50 IU 2 $h^{-1}$) to prevent clotting.

Intracavernous injection In 48 rabbits, divided into 2 groups, 8 animals in each group for one dose, KMUP-1 and sildenafil (0.2, 0.4, 0.6 mg $kg^{-1}$) were, respectively, injected into CCSMs in a volume of less than 0.2 ml. Normal saline in increasing volumes (0.05, 0.1, 0.2 ml) was injected in four rabbits as a control group. The effects of KMUP-1 and normal saline on the intracavernous pressure (ICP) and on the duration of action were evaluated. In order to minimize the effect of the previous drug, the cavernous body was flushed with 0.2 ml normal saline before each injection and the time interval between each injection was at least 1.5 h.

Statistical evaluation of data The results are expressed as mean ±s.e.mean. Statistical differences were determined by independent and paired Student's t-test in unpaired and paired samples, respectively. Whenever a control group was compared with more than one treated group, the one way ANOVA or two way repeated measures ANOVA was used. When the ANOVA manifested a statistical difference, the Dunnett's or Student-Newman-Keuls test was applied. The P value less than 0.05 was considered to be significant in all experiments. Analysis of the data and plotting of the figures were done with the aid of software (SigmaStat and SigmaPlot, Version 5.0, San Rafael, Calif., U.S.A.) run on an IBM compatible computer.

EXAMPLE 1

Synthesis of Compound A (N7-bromoethyl theophylline)

Dissolve 0.2 mole theophylline (1,3-dimethylxanthine) into 0.4 mole dibromoethane in a glass reactor, followed by boiling and mixing at 100° C. on mantle heater and refluxed for 4 hours, equipped with a cooling condenser to return the vaporized solvent. Till solid completely melt, then added with 125 ml 1.6 N NaOH as catalyst to react under 100° C. and boiling for overnight, leading white solid precipitated and NaBr soluble in upper water layer. The white solid precipitate was filtered, dissolved in methanol, concentrated under reduced pressure to obtain white coarse crystal, and then recrystallized with methanol to obtain the pure white crystal compound A (N7-bromoethyl-3 methyl-1-methylxanthine, N7-bromoethyl theophylline) (see scheme of synthesis).

EXAMPLE 2

Synthesis of Compound B (N7-bromoethyl IBMX)

Dissolve 0.2 mole 3-isobutyl-1-methylxanthine (IBMX) into 0.4 mole dibromoethane in a glass reactor, followed by boiling and mixing at 100° C. on mantle heater and refluxed for 4 hours, equipped with a cooling condenser to return the vaporized solvent. Till solid completely melt, then added with 125 ml 1.6 N NaOH as catalyst to react under 100° C. and boiling for overnight, leading white solid precipitated and NaBr soluble in upper water layer. The white solid precipitate was filtered, dissolved in methanol, concentrated under reduced pressure to obtain white coarse crystal, and then recrystallized with methanol to obtain the pure white crystal compound B (N7-bromoethyl IBMX).

EXAMPLE 3

Synthesis of Theophylline-based Derivatives (KMUPs) from Compound A

Compound A dissolved in methanol, according to targeting products required, was added with 1-(2-Chlorophenyl) piperazine (in compound 1), 1-(m-Chlorophenyl) (in compound 2 piperazine, 1-(4-Nitrophenyl) piperazine (in compound 4), and 1-(o-Metyhoxyphenyl) piperazine (in compound 8), respectively, to processes the amination, using NaOH as catalyst, and reflux for 4 hours in methanol to precipitate, to dissolve the solid product, and to recrystallize with methanol to obtain compounds (see scheme of synthesis).

EXAMPLE 4

Synthesis of Theophylline-based Compound from Compound B

Follow the process of example 1, replace Compound A (N7-bromoethyl theophylline) with Compound B (N7-bromoethyl IBMX), respectively, to obtain derivated compounds.

EXAMPLE 5

Formulation of Tablet Form

| | | |
|---|---|---|
| KMUP-1 analogues | 50 mg | |
| Lactose | 30 mg | |
| Starch | 4 mg | |
| magnesium stearate | 6 mg | |
| Corn starch | 10 mg | |

The prescription as above can be prepared a tablet that contains KMUPs (KMUP-1 analogues)

TABLE 1

The physicochemical Data of N7-substituted theophylline

| Compound | $MS_{(Scan\ FAB+)}$ | $^1$H-NMR($CDCl_3$) |
|---|---|---|
| 1 (KMUP-1) | 402.88 | δ 3.60(s, 3H, $NCH_3$), 3.42(s, 3H, $NCH_3$) 4.45(t, 2H, $NCH_2$), 2.85(t, 2H, $NCH_2$) 2.70(t, 4H, $2×CH_2$), 3.04(t, 4H, $2×CH_2$) 6.97–7.01(m, 2H, 2×Ar—H), 7.27–7.36(m, 2H, 2×Ar—H), 7.69(s, 1H, imidazole-H) |
| 8 (KMUP-2) | 398.46 | δ 3.42(s, 3H, $NCH_3$), 3.61(s, 3H, $NCH_3$) 2.89(t, 2H, $NCH_2$), 4.49(t, 2H, $NCH_2$) 2.75(t, 4H, $2×CH_2$), 3.09(t, 4H, $2×CH_2$) 3.86(s, 3H, $OCH_3$), 6.88–7.06(m, 4H, 4×Ar—H) 7.72(s, 1H, imidazole-H) |
| 3 (KMUP-3, ortho-$NO_2$) | 413.44 | δ 3.60(s, 3H, $NCH_3$), 3.42(s, 3H, $NCH_3$) 4.45(t, 2H, $NCH_2$), 2.85(t, 2H, $NCH_2$) 2.70(t, 4H, $2×CH_2$), 3.40(t, 4H, $2×CH_2$) 6.82(m, 2H, 2×2 x Ar—H), 8.10(m, 2H, 2×Ar—H) 7.69(s, 1H, imidazole-H), |
| 4 (KMUP-4, para-$NO_2$) | 413.44 | δ 3.55(s, 3H, $NCH_3$), 3.45(s, 3H, $NCH_3$) 4.40(t, 2H, $NCH_2$), 2.80(t, 2H, $NCH_2$) 2.60(t, 4H, $2×CH_2$), 3.00(t, 4H, $2×CH_2$) 6.90–7.11(m, 2H, 2×Ar—H) 7.60–7.78(m, 2H, 2×Ar—H) 7.40(s, 1H, imidazole-H), |

TABLE 2

Peak increased intracavernous pressure (DICP) and duration of tumescence respone to KMUP-1 and sildenafil (n = 8)

| | ΔICP (mmHg) | | DT (min) | |
|---|---|---|---|---|
| Doses (mg/kg) | KMUP-1 | Sildenafil | KMUP-1 | Sildenafil |
| 0.2 | 30 ± 5.25 | 28 ± 3.21 | 15 ± 2.24 | 19 ± 3.32 |
| 0.4 | 55 ± 6.21 | 32 ± 4.05 | 27 ± 2.05 | 24 ± 3.45 |
| 0.6 | 67 ± 12.32 | 40 ± 11.05 | 35 ± 3.45 | 28 ± 4.59 |
| Vehicle | 8 ± 2.11 | | 0.4 ± 0.2 | |

ICP (mmHg) = intracavernous pressure
DT = duration of tumescence.
All injection volumes of KMUP-1, sildenafil and vehicle were 0.2 ml. The basal value of ICP recorded was 13.3 ± 2.6 mmHg (n = 6).

What is claimed is:

1. A method for inducing corpus cavernosal relaxation activity, which comprises:

administering to a mammal in need thereof, a pharmaceutically effective amount of a compound of formula (II) and a pharmaceutically effective carrier,

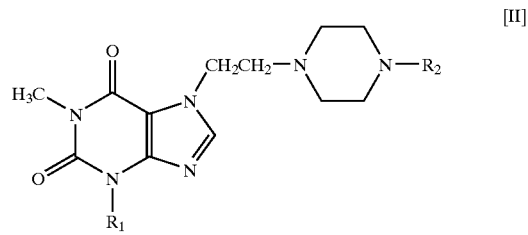

[II]

where $R_1$ is —$CH_3$ or —$CH_2CH(CH_3)_2$, and $R_2$ is

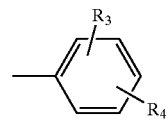

where $R_3$ and $R_4$ are independently selected from the group consisting of $OCH_3$, $CH_3$, $NO_2$, F, Cl, Br and I, wherein the compound has been synthesized from theophylline (1-methyl, 3-methyl xanthine) or IBMX (1-methyl-3-isobutyl xanthine).

2. A method for inducing corpus cavernosal relaxation activity, which comprises:

administering to a mammal in need thereof, a pharmaceutically effective amount of a compound of formula (I) and a pharmaceutically effective carrier,

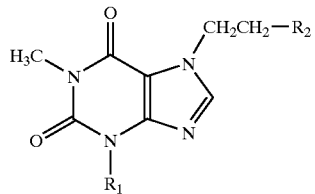
[I]

where $R_1$ is —$CH_3$ or —$CH_2CH(CH_3)_2$, and $R_2$ is

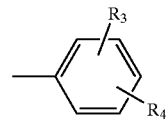

where $R_3$ and $R_4$ are independently selected from the group consisting of $OCH_3$, $CH_3$, $NO_2$, F, Cl, Br and I, wherein the compound has been synthesized from theophylline (1-methyl, 3-methyl xanthine) or IBMX (1-methyl-3-isobutyl xanthine).

* * * * *